(12) United States Patent
Lewis et al.

(10) Patent No.: US 11,286,457 B1
(45) Date of Patent: Mar. 29, 2022

(54) METHODS OF IMPROVED YEAST HEALTH AND FERMENTATION WITH UREASE

(71) Applicant: POET Research, Inc., Sioux Falls, SD (US)

(72) Inventors: Stephen M. Lewis, Sioux Falls, SD (US); Camille K. Crouch, Hartford, SD (US); Benjamin P. Gacke, Baltic, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 16/543,115

(22) Filed: Aug. 16, 2019

Related U.S. Application Data

(60) Provisional application No. 62/764,913, filed on Aug. 16, 2018.

(51) Int. Cl.
| | |
|---|---|
| *C12N 9/80* | (2006.01) |
| *C12N 1/16* | (2006.01) |
| *C12P 7/06* | (2006.01) |
| *C12P 7/64* | (2022.01) |
| *C12C 11/09* | (2006.01) |
| *C12C 5/00* | (2006.01) |

(52) U.S. Cl.
CPC .................. *C12N 1/16* (2013.01); *C12C 5/00* (2013.01); *C12C 5/004* (2013.01); *C12C 11/09* (2013.01); *C12N 9/80* (2013.01); *C12P 7/06* (2013.01); *C12P 7/64* (2013.01); *C12Y 305/01005* (2013.01)

(58) Field of Classification Search
CPC .... C12N 9/80; C12N 1/16; C12Y 305/01005; C12P 7/06; C12P 7/10
See application file for complete search history.

(56) References Cited

FOREIGN PATENT DOCUMENTS

WO    WO2009089103    *    7/2009

OTHER PUBLICATIONS

Bayrock. May 19, 2017; Protease use for FAN as urea substitute poses challenges (on the world wide web at ethanolproducer.com/articles/14321/protease-use-for-fan-as-urea-substitute-poses-challenges. pp. 1-2.*
Damiano et al. 1985; Improvements in ethanol concentration and fermenter ethanol productivity in yeast fermentations using whole soy flour in batch and continuous recycle systems. Biotechnol. Lett. 71: 2001-2006.*
DeMoura et al. 2011; Pilot-plant proof-of-concept for integrated, countercurrent, two-stage, enzyme-assisted aqueous extraction of soybeans. J. Am. Oil. Chem. Soc. 88:1649-1658.*
Martinelli et al. 2017; Soybean ubiquitous urease with purification facilitator: An addition to the moonlighting studies toolbox. Process Biochemistry. 52:245-258.*
Sigma Aldrich, 2021. Product Information Urease Type III; www.sigmaaldrich.com/deepweb/assets/sigmaaldrich/product/documents/382/636/u1500dat.pdf.*
Feder et al. 2021; Temperature-dependent inactivation and catalysis rates of plant-based ureases for engineered biomineralization. Engineering Reports. D122299, pp. 1-14.*
Balakumar (2012) "Osmo Thermo and Ethanol Tolerances of *Saccharomyces cerevisiae* S1" Braz J Microbiol. 43(1):157-166.
Chin (2012) "Bactericidal Activity of Soymilk Fermentation Broth by In Vitro and Animal Models" J Med Food. 15(6):520-6.
Jimenez-Marti and del Olmo (2008) "Addition of ammonia or amino acids to a nitrogen-depleted medium affects gene apxression patterns in yeast cells during alcoholic fermentation" FEMS Yeast Research 8(2):245-256.
Khan et al. (2013) "Kinetics and Thermodynamic Study of Urease Extracted from Soybeans" Biologia, Pakistan, 59(1):7-14.
Kitagawa et al. (2008) "Effect of Soy Peptide on Brewing Beer" J Biosci Bioeng. 105(4):360-6.
Mielenz (2009) "Fermentation of soybean hulls to ethanol while preserving protein value" Bioresource Technology 100(14):3532-3539.
Nichols (2005) "Ethanol Fermentation of Starch from Field Peas" Cereal Chem 82(5):554-558.
Nichols (2011) "Conversion of starch from dry common beans (*Phaseolus vulgaris* L.) to ethanol" Industrial Crops and Products 33:644-647.
Polacco (1979) "Comparisons of soybean urease isolated from seed and tissue culture" Journal of Biological Chemistry 254(5):1707-15.
Pradeep (2010) "High Gravity Fermentation of Sugarcane Molasses to Produce Ethanol: Effect of Nutrients" Indian J Microbiol., 50(Suppl 1):82-87.
Sekhon (2015) "Effect of co-products of enzyme-assisted aqueous extraction of soybeans on ethanol production in dry-grind corn fermentation" Bioresource Technology, 192:451-460.
Sirko (2000) "Plant ureases: roles and regulation" Acta Biochimica Polonica 47(4):1189-1195.
Song (2008) "Immunoreactivity reduction of soybean meal by fermentation, effect on amino acid composition and antigenicity of commercial soy products" Food Chemistry, 108(2 15):571-581.
Thomas and Ingledew (1990) "Fuel alcohol production: effects of free amino nitrogen on fermentation of very-high-gravity wheat mashes" Appl Environ Microbiol. 56(7):2046-50.
Van Der Ven (2005) "Inactivation of Soybean Trypsin Inhibitors and Lipoxygenase by High-Pressure Processing" Journal of Agricultural and Food Chemistry 53(4):1087-92.
Viegas (1985) "Nutrient Enhanced Production of Remarkably High Concentrations of Ethanol by *Saccharomyces bayanus* through Soy Flour" Applied and Environmental Microbiology 50(5):1333-5.

(Continued)

*Primary Examiner* — Karen Cochrane Carlson
(74) *Attorney, Agent, or Firm* — FisherBroyles, LLP; Cara L. Crowley-Weber; Cary Reeves

(57) ABSTRACT

Methods, compositions, and systems for propagation and fermentation, particularly large scale operations for production of ethanol and dried distiller's grain are provided. Addition of urease and urea to propagation and/or fermentation improves yeast health, fermentation efficiency, and quality and quantity of DDG. Urease can be in reagent form or can be endogenous to the natural feedstock.

20 Claims, 19 Drawing Sheets

(56) References Cited

OTHER PUBLICATIONS

Yao (2011) "Effect of soy skim from soybean aqueous processing on the performance of corn ethanol fermentation" Bioresource Technology 102(19):9199-9205.

Yao (2012) "Effects of fermentation substrate conditions on corn-soy co-fermentation for fuel ethanol production" Bioresource Technology 120:140-148.

* cited by examiner

Amino and protein profiles of corn, soy flour, dehulled soy flour, and blends

|  | Soy Inclusion | Corn Inclusion | Methionine %DMB | Lysine %DMB | Crude Protein |
|---|---|---|---|---|---|
| Corn | 0.0% | 100.0% | 0.16 | 0.31 | 8.72 |
| Soy Flour | 100.0% | 0.0% | 0.55 | 2.77 | 43.90 |
| Soy Flour | 10.0% | 90.0% | 0.21 | 0.57 | 12.59 |
| Soy Flour | 5.0% | 95.0% | 0.18 | 0.45 | 10.71 |
| Soy Flour | 2.5% | 97.5% | 0.17 | 0.39 | 9.58 |
| De-hulled Soy Flour | 100.0% | 0.0% | 0.57 | 2.80 | 44.27 |
| De-hulled Soy Flour | 10.0% | 90.0% | 0.18 | 0.55 | 12.72 |
| De-hulled Soy Flour | 5.0% | 95.0% | 0.20 | 0.48 | 11.00 |
| De-hulled Soy Flour | 2.5% | 97.5% | 0.16 | 0.35 | 9.43 |

Figure 10

METHODS OF IMPROVED YEAST HEALTH AND FERMENTATION WITH UREASE

CROSS-REFERENCE TO RELATED APPLICATIONS

This application claims priority under 35 U.S.C. 119(e) to U.S. Provisional Patent Application Ser. No. 62/764,913, filed Aug. 16, 2018, the disclosure of which is hereby incorporated by reference in its entirety.

FIELD

Provided herein are methods, compositions, and systems for propagation and fermentation, particularly in large scale operations for production of ethanol and dried distiller's grain.

BACKGROUND

Industrial fermentation involves the breakdown of a feedstock by a microorganism, e.g. yeast and bacteria, into one or more products. In addition to the feedstock, other nutrients may be provided to the organism to facilitate the fermentation. For example, a traditional ethanol fermentation process utilizes grain-based feedstocks (e.g., corn, sorghum/milo, barley, wheat, etc.), or other sugar sources (e.g., sugar cane, sugar beets, etc.). Enzymes, whether endogenous to the grain, added to the fermenter, or produced by yeast, convert components of the feedstock into simple sugars. Yeast, acting subsequent to or simultaneously with the enzymes, convert the simple sugars to ethanol and carbon dioxide.

To identify alternative sources of protein for yeast, Yao et al. (Bioresource Technology 120:140-148, 2012), replaced water with soy skim in fermentations. Section 2.4 mentions heating a mixture of soy skim and corn to 76° C. (approximately 168.8° F.) for 2 hours then cooling to 30° C. before adjusting pH, adding yeast, glucoamylase, lactrol and urea. "Urea was added to the fermentation media in most studies except for those described in Sections 2.7 and 3.3, in which the effect of nitrogenous nutrient adequacy was examined."

Yao et al. theorized that soy skim could supply all the needed nitrogen and that urea would be unnecessary at 100% soy skim inclusion. Fermentations with or without urea gave the same growth rates (as measured by maximum production rate of carbon dioxide) when 100% skim replacement was used. When only 20% soy skim was used, the rate without added urea was lower than when urea was added indicating that 20% skim replacement had inadequate nitrogenous nutrients for yeast growth. However, "no significant difference in total ethanol yield was found between the treatments with or without urea". See Yao et al. at section 3.3.

Yao et al. also discussed work by other authors with mixed results for rate and titer. On page 145, last paragraph of section 3.2, it mentions that Viegas (1985) "suggested that the mechanism of soy flour enhancement of the fermentation performance was nutrient satisfaction." Yao et al. also attributes the results to the nutrient value of the soy skim: "The easily utilizable nitrogenous matters (i.e., the nature of nitrogen sources) for yeast and possibly the minor nutrients, such as minerals and vitamins present in soy skim, are likely the main reasons for the rapid fermentation. Soy skim contained considerable amounts of free amino acids and small peptides, some of which were the amino acids favorably utilized by yeast (Yao et al., 2011). These amino nitrogen sources may be utilized faster by yeast (Kitagawa et al., 2008), enable the yeast to consume the carbon skeleton from amino acids (Thomas and Ingledew, 1990), and increase protein biosynthesis in yeast cells (Jimenez-Marti and del Olmo, 2008)."

There is a need to identify and explore procedures for efficient microorganism propagation and fermentation.

BRIEF SUMMARY

Provided herein are compositions, methods, and systems for propagation and fermentation, for example, fermentation used in the production of bioethanol.

Provided herein are compositions comprising a primary feedstock, urease, urea, a microorganism, and water. The primary feedstock comprises the sugar source for propagation and fermentation by the microorganisms.

The urease can be in reagent form, or can be produced by microbes and/or by plants and can be present in the composition by adding, for example, the urease producing microbe or feedstock containing the urease produced by the plant. In some embodiments, the urease is a reagent. The urease can be endogenous to a feedstock, for example, a urease containing feedstock. The urease containing feedstock can be an agricultural feedstock, e.g. a plant source of urease. In some embodiments, the urease containing feedstock is a legume. In some embodiments, the urease containing feedstock can be soybean seeds (e.g. *Glycine max*), jack bean seeds (e.g. *Canavalia ensiformis*) and/or winged bean seeds (e.g. *Psophocarpus tetragonolobus*). In some aspects, the urease containing feedstock is sourced from soybean, for example, enzyme active soy flour or soybean hull. The soybean can be uncooked.

In some embodiments, urease can be obtained from a microorganism which naturally produces urease or a microorganism engineered to produce urease, for example, naturally occurring or genetically engineered yeast or bacteria. Likewise, it is contemplated herein that plants used as a primary starch source in propagations and fermentations can be genetically modified to produce urease.

In some embodiments, the composition comprises about 90.00% to about 100.00% w/w milled corn grain as the primary starch feedstock and about 0.00% to about 10.00% w/w urease containing feedstock.

The composition can further comprise one or more fiber degrading enzymes (e.g. cellulases and/or hemicellulases) and/or other enzymes (e.g. lipases, proteases, and/or phytases). In some aspects, one or more of a cellulase, lipase, protease, and phytase is present in the fermenter.

The propagation and/or fermentation microorganism can be yeast or bacteria or both yeast and bacteria. This same microorganism can be genetically modified to produce urease and as such, is the source of urease present in the composition.

Provided herein are methods of improving fermentation efficiency. In some aspects the methods comprise: (a) combining a feedstock, urease, urea, a microorganism, and water in a fermenter; and (b) fermenting the feedstock. The fermentation efficiency is improved relative to the fermentation efficiency achieved in the absence of urea and urease.

The improved fermentation efficiency can provide at least one benefit selected from the group consisting of: (a) increased ethanol production; (b) decreased residual starch; (c) increased quantity of dried distillers grains or dried distillers grains with solubles (both referred to herein as dried distillers grains or DDG); (d) higher protein content DDG; (e) improved essential amino acid profile of DDG; (f)

increased oil recovery; (g) decreased DDG pigmentation; and (h) increased fiber conversion.

In some aspects, the benefit is increased oil recovery. In some aspects, the increased oil recovery is achieved with minimal increase in drop solids.

In some aspects, the benefit is higher protein content DDG. In some aspects, the higher protein content DDG is achieved without a concurrent increase in non-protein nitrogen (NPN).

In some aspects, the benefit is an improved essential amino acid profile of DDG. The DDG can contain increased levels of one or more amino acids. For example, by including soy, the DDG can contain increased levels of one or more amino acids which are more prevalent in soy than in corn such as arginine, aspartic acid, glutamic acid, histidine, and hydroxylysine, hydroxyproline, isoleucine, leucine, lysine, methionine, ornithine, phenylalanine, proline, serine, threonine, tryptophan, and tyrosine.

Provided herein are methods of increasing ethanol produced from fermentation. The methods comprise: (a) combining urease and/or about 90.00% to about 100.00% w/w milled corn grain, about 0.00% to about 10.00% w/w urease containing feedstock, yeast, urea, and water in a fermenter; (b) fermenting the feedstock to produce beer. The ethanol recovered from the beer is increased relative to the ethanol recovered from beer produced by fermentation of corn in the absence of urease. The urease containing feedstock can be soybean seeds (e.g. *Glycine max*), jack bean seeds (e.g. *Canavalia ensiformis*) and/or winged bean seeds (e.g. *Psophocarpus tetragonolobus*). In some embodiments, the microorganism used in fermentation is engineered to produce urease.

In some aspects, the urease (or urease producing microorganism or urease containing feedstock) and urea are added after fermentation has been initiated.

Provided herein are methods of improving yeast health and/or performance comprising adding urease to a fermenter or propagation tank. The urease can be added prior to corn milling, during corn milling, after corn milling, during propagation, and/or during fermentation. In some aspects, the urease is endogenous to a urease containing feedstock, e.g. soybeans (for example, raw, uncooked, enzyme active, de-hulled soy flour, e.g. *Glycine max*), jack bean seeds (e.g. *Canavalia ensiformis*) and/or winged bean seeds (e.g. *Psophocarpus tetragonolobus*). In some aspects, the urease is added as a reagent. In some embodiments, the microorganism is engineered to produce urease.

The soybeans can include, for example, whole soybean, soybean flour, de-hulled soybean, de-hulled soy flour or combinations thereof.

Provided herein are compositions comprising (DDG). In some aspects, the DDG exhibits: (a) higher protein content; (b) improved essential amino acid profile; (c) decreased pigmentation; and/or (d) antibacterial activity. The improved characteristics of the DDG are relative to the characteristics exhibited by DDG obtained from fermentation performed in the absence of soy, urease, and/or urea.

Other objects and advantages will become apparent from a review of the ensuing detailed description.

BRIEF DESCRIPTION OF THE FIGURES

FIG. 10 is a chart showing increased amino acids in soy (and de-hulled soy flour) relative to corn, as well as the amino acid content of soy/corn and de-hulled soy flour/corn mixtures. Soybeans have a much higher lysine, methionine, and tryptophan content than corn. These are 3 of the main essential amino acids used for feed formulations.

FIG. 11 depicts increased fat content for DDG or extraction after fermentation using soy and corn, relative to fat content using corn only.

DESCRIPTION

Figure 1:
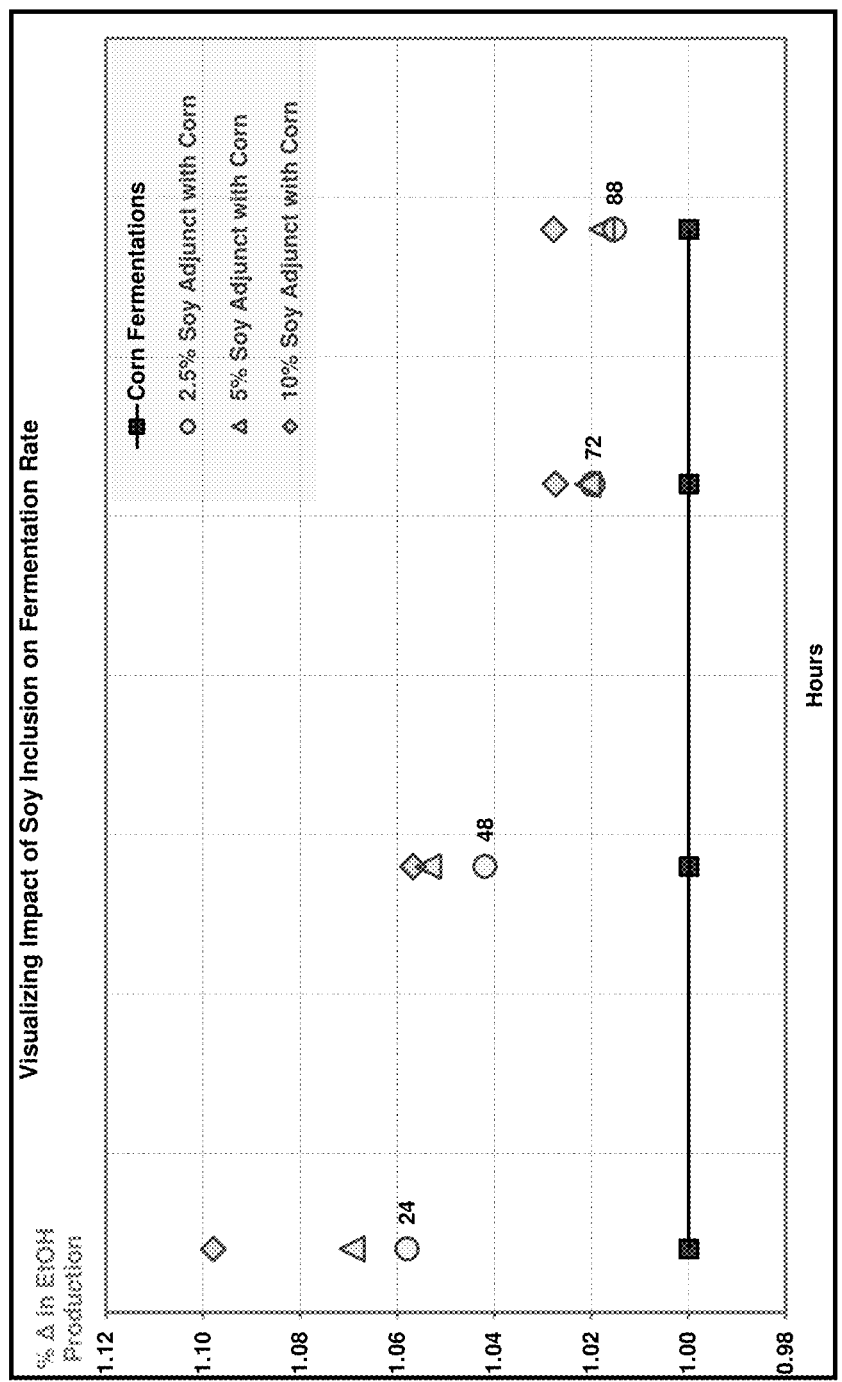
FIG. 1 shows the change in ethanol titer compared to a corn-only control as soy flour (enzyme active de-hulled full fat soy flour) is included into corn fermentations. Three different soy inclusion amounts were analyzed. Amount of corn solids was kept constant such that the starch contained within each fermenter was the same. This data shows that there is more of an increase at the earlier hours of fermentations providing evidence for a faster rate of fermentation using soy in corn fermentations.

It is to be understood that this invention is not limited to particular compositions, systems, methods, and experimental conditions described, as such compositions, systems, methods, and conditions may vary. It is also to be understood that the terminology used herein is for the purpose of describing particular embodiments only, and is not intended to be limiting, since the scope of the present disclosure will be limited only by the appended claims.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

In a typical ethanol production plant, corn, or other suitable primary feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, can be used in the methods and compositions provided herein.

The ground corn or other primary feedstock may be combined with water to form a slurry, and the pH of the slurry mixture may be adjusted as needed. A microorganism, for example, a yeast such as *S. cerevisiae*, is added. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. Other desired components can be added to the fermenter, including certain enzymes which produce monomeric sugars from polymeric sugars (e.g. glucose from starch) in the fermentable solids as in simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

The slurry can be held at specified temperatures to facilitate the production of ethanol for a determined period of time. Fermenting can include contacting a mixture including sugars from the reduced plant material (e.g., fractionated plant material) with yeast under conditions suitable for growth of the yeast and production of ethanol. During fermentation, the yeast converts the sugars (e.g. glucose) to ethanol and carbon dioxide, and between the enzymatic production of sugars (e.g. glucose) and the fermentation process, sugars (e.g. glucose) may be maintained in the system at a low steady state. After fermentation, further treatment and/or distillation is performed to recover the ethanol, oil, carbon dioxide, dried distiller's grains (DDG), and/or other co-products.

It has been determined and disclosed herein that addition of urease and urea can be beneficial to propagation and fermentation. As such, provided herein are compositions, methods, and systems for propagation and fermentation utilizing urease and urea. It has also been determined and disclosed herein that addition of soybean to feedstock (or any other urease-containing feedstock) can be beneficial to propagation and fermentation. As such, provided herein are compositions, methods, and systems for propagation and fermentation using soybean as a percentage of total feedstock.

Ureases are nickel-containing metalloenzymes of high molecular weight that catalyze the hydrolysis of urea into carbon dioxide and ammonia:

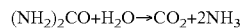

The hydrolysis of urea occurs in two steps. First, ammonia and carbamate are produced, then carbamate immediately hydrolyzes to ammonia and carbonic acid. Urease activity increases the pH of its environment as it produces ammonia.

In the compositions, methods, and systems provided herein, urease can be sourced as a reagent and added to the propagation and/or fermentation tanks. In the compositions, methods, and systems provided herein, urease can be endogenous to a plant source, such as, for example, soybean seeds (e.g. *Glycine max*), jack bean seeds (e.g. *Canavalia ensiformis*), winged bean seeds (e.g. *Psophocarpus tetragonolobus*), and/or any other urease-containing feedstock. Any aspect of the disclosure herein can use jack bean seeds and/or winged bean seeds as a feedstock rather than soybean or soy flour. Likewise, urease reagent can be used in place of a urease-containing feedstock in an amount sufficient to achieve the desired effect. A urease producing microorganism can be used herein as a source of urease.

A by-product of enzyme-assisted aqueous extraction of soybeans, soy skim is a protein rich liquid containing only a fraction of total soy nutrients. Replacing water with soy skim in conventional corn starch fermentations has been found to increase fermentation rate and produce higher amino acid content DDG but without effect on ethanol production. In a conventional fermentation process, however, feedstock is subject to high temperatures that denature enzymes and amino acids. Endogenous enzymes, for example, are denatured above 160° F.

Years of commercial and scientific efforts have optimized corn fermentation. Addition of soy to an already optimized propagation or fermentation would be expected to decrease ethanol production since non-fermentable components from the soy inclusion would replace some of the corn starch used in fermentation.

In addition, legumes such as soy contain anti-nutritional factors that are unpalatable or undigestible, and sometimes even toxic. Such anti-nutritional factors include non-protein amino acids, quinolizidine alkaloids, cyanogenic glycosides, pyrimidine glycosides, isoflavones, tannins, oligosaccharides, saponins, phytates, lectins, and protease inhibitors. Fermentation can help minimize or eliminate anti-nutritional factors in soy.

It has been determined herein that utilizing enzyme active soybean at 10% or less of the total feedstock in combination with added urea provides exceptional value in the corn to ethanol process. Unexpectedly, adding soy or urease in combination with urea to the fermentation process and/or the propagation process increases ethanol production, in addition to other surprising benefits, without adding non-protein nitrogens (NPNs) to the DDG. While not wishing to be held to theory, the mechanism involves enzymes present in the soy, e.g. urease, which remain active as the feedstock is not subjected to denaturing temperatures.

In some instances, feedstocks are subjected to non-denaturing temperatures during the starch to ethanol process. According to embodiments provided herein, the feedstock is not exposed to temperatures that will denature the endogenous enzymes and amino acids. For example, the feedstock added to a propagation tank or fermentation tank is not exposed to temperatures greater than 160° F. (71° C.). A low temperature starch to ethanol process is contemplated as useful herein. However, urease can be added to the starch to ethanol process in a system utilizing higher temperatures, as long as the urease is added after the propagation tank or fermentation tank has cooled below the denaturation temperature of the urease, e.g. in some embodiments below at least to 160° F. (71° C.). For example, in some systems, urease can be added to the cooled propagation slurry in preparation for fermentation, in other words, if enzyme additions occur after cooling of a liquefied starch in a cooked starch process.

Soybean, whole soybean, enzyme-active soy flour, and dehulled soybean can be used in the compositions, methods, and systems provided herein, and can be used interchangeably except when context dictates otherwise.

Provided herein are compositions comprising 0.05%-10% w/w, for example, 1%, 2.5%, 5%, or 7.5%, soybean in corn starch fermentations, in embodiments where soybean is the urease source. The desired amount of urease is any amount useful in catalyze the hydrolysis of urea present in the system into carbon dioxide and ammonia. The urease can be added in reagent form in a dose equivalent to the amount of urease present in 0.05%-10% w/w soybean in corn starch fermentations. Urease is present in soy in amounts ranging from about 50 units per gram of soy to about 100 units per gram of soy, for example, about 86 units per gram of soy. As such, urease in reagent form (or as produced by a microorganism) can be included or added to the composition as an equivalent dose or an equivalent dose that provides a similar urea conversion rate to the urease contained in an amount of soy feedstock included in the propagation and/or fermentation.

Khan et al., (Biologia, Pakistan, 2013, 59(1): 7-14) mention 86.8 units of urease activity per gram of soy, at a Khan index of 30° C. and a pH 8 after 30 seconds of incubation. These calculations are useful in determining the amount of urease that can be added in reagent form to the propagations and/or fermentations described herein.

TABLE 1

| Calculated urease levels in soy | | |
| --- | --- | --- |
| KHAN 2013 | 86.8 | unit urease/g soy |
| Soy Inclusion Assume 36% solids | | |
| % Soy inclusion in feedstock | g soy | Urease units per g total feedstock |
| 0 | | |
| 0.05% | 0.018 | 0.04 |
| 0.10% | 0.036 | 0.09 |
| 0.50% | 0.18 | 0.43 |
| 1% | 0.36 | 0.87 |
| 2.50% | 0.9 | 2.17 |
| 5% | 1.8 | 4.34 |
| 10% | 3.6 | 8.68 |

As such, compositions herein can comprise urease in amounts from about 0.04 units per gram of total feedstock to about 10 units per gram of total feedstock, or about 1 unit per gram of total feedstock to about 9 units per gram of total feedstock, or about 2 units per gram of total feedstock to about 8 units per gram of total feedstock, or about 4 units per gram of total feedstock to about 8 units per gram of total feedstock, or any amount within these ranges, such as about 0.4 units, about 0.5 units, about 1 unit, or about 2 units, or about 3 units, or about 4 units, or about 5 units, or about 6 units, or about 7 units, or about 8 units, or about 9 units, or about 10 units per gram of total feedstock.

Compositions containing urease are useful in fermentations utilizing raw starch hydrolyzing enzymes and conventional fermentations (where the urease is added after liquefying the starch, when the slurry has been cooled in a cook process) and have surprising effects in propagation and fermentation, as well as surprising benefits to the by-products of fermentation. For example, the increase in fiber conversion to ethanol is surprising, and the resulting DDG with higher levels of protein from the soy is beneficial for livestock consumption (relative to a 48% soy product containing the antinutritional factors associated with soy).

Urease can be added as endogenous to a feedstock, e.g. soy flour, as produced by a microorganism, e.g. a genetically modified yeast or bacteria, or as a reagent.

Adding low levels of soy flour in combination with urea in yeast propagations improves yeast health evidenced by increased yeast cell numbers and larger yeast cell size. The increase in cell numbers can range from about 3% to about 8%; the average yeast cell size can be increased by about 5% to about 10% relative to propagation with corn flour and urea but in the absence of urease. In addition, including low levels of soy flour in combination with urea into corn starch fermentations by mixing soy flour or soy flour extract containing active enzymes into corn mash increases fermentation rates, as well as produces higher ethanol titers and lower residual starch numbers at the end of fermentations. For the DDG co-product from the corn to ethanol process, production amount as well as the protein content increases. While not wishing to be held to theory, it is believed that the addition of urease during propagation, results in healthier GMO yeast which express more starch hydrolyzing enzymes that break down starch for use by the yeast during fermentation. The higher starch conversion contributes to greater amounts of ethanol produced.

Dehulled, enzyme active, full fat soy flour only contains about 8-10% carbohydrate in the form of sucrose, raffinose, and stachyose. Alpha-galactosidase is needed to break down these sugars to glucose available for fermentation and it is contemplated herein that it can be added to propagation and/or fermentation systems to further increase ethanol production.

It is contemplated herein that soy can be present as a percentage of the total feedstock in an amount less than or equal to about 10% w/w, or from about 0.05% w/w to about 10.00% w/w of the total feedstock, for example, about 2% or about 2.5% w/w to about 7.5% or about 8% w/w, or about 5% w/w, or about 5% w/w to about 7.5% w/w, or about 7.5% w/w to about 10% w/w, of the total feedstock. Compositions, systems, and methods provided herein use enzyme active soy (such as soy flour or soy extract) in such amounts. Low temperature fermentation processes, such as raw starch utilizing processes, are preferred where urease is added directly to feedstock or feedstock slurry as they avoid the denaturing temperatures of a cooked starch process. Alternatively, the urease can be added after a cooked slurry has been cooled below enzyme degrading temperatures. It is contemplated herein that urease can be present in the composition in an amount equivalent to the amount of urease found in soy at 0.5% to 10% of the total feedstock.

Urea, as a 50% aqueous solution, is commonly added to commercial fermentation systems in an amount of about 600 gallons in a 550,000 gallon fermentation tank, or about 622 ppm. Propagation vats can contain about 1000 ppm urea. Greater amounts of urea, such as, for example, 1200 gallons in a 550,000 gallon fermentation tank, leave excess urea present in the DDG. The excess urea is considered non-protein nitrogen (NPN) and artificially raises crude protein values. In large amounts, the presence of NPN is considered an undesirable adulteration of DDG proteins. Surprisingly, as described herein, larger amounts of urea can be used in fermentation and propagation if urease is included in the fermentation and/or propagation tanks. Including urease ensures less residual urea to contribute to NPN. It is contemplated herein that urea can be present in propagation or fermentation in an equivalent amount up to about 3200 ppm when urease is employed. As used herein, when referring to gallons of urea it is an equivalent to gallons of 50% urea solution.

Yeasts useful according to the embodiments described herein are any yeasts typically useful in converting feedstock into ethanol, especially in an industrial setting. Such yeasts may include, e.g., various strains of *Saccharomyces cerevisiae* such as, non-genetically modified commodity yeasts; consolidated bioprocessing yeasts (CBP, expressing glucoamylase and/or alpha-amylase); yeast genetically modified for various purposes; a genetically modified yeast blend; and a genetically modified thermotolerant yeast.

New strains of Consolidated BioProcessing (CBP) yeast have been identified that require higher levels of urea as well as higher pH for optimum performance compared to previous commodity (non-GMO) yeast strains. However, yeast strains do not produce extracellular urease. By adding enzyme active soy into such fermentations along with higher levels of urea, the endogenous urease in soy converts urea into ammonia and carbon dioxide. This transformation increases fermentation pH as ammonia levels increase. Ammonia also provides nitrogen for yeast health. Conversion of urea to ammonia in situ is preferred to on site storage and dispensing of bulk ammonia since bulk ammonia is dangerous to work with. The use of enzyme active soy results in a final feed product with increased protein without the presence of non-protein nitrogen in the DDG. For example, the addition of a small amount of soy, e.g. less than or equal to about 10% w/w soy in the total feedstock, can increase the protein content of the final DDG due to the inclusion of the soy protein. In addition, it permits the inclusion of more urea that is converted by the yeast to increased protein content and DDG volume by increasing yeast cell mass. Yeast cell volume is a product of both production increase and improved health of existing cells (size and weight).

Inclusion of soy can also lead to increased conversion of fiber to ethanol. For example, other endogenous enzymes in soy, such as hemicellulases, are active in breaking down fiber not only in soy but also, surprisingly, in corn, into component sugars. These enzymes as well as others present in soy assist in making fiber available for degradation by endogenous cellulases present in corn and soy. These enzymes help to break down the complex structure of the fiber; any enzyme that helps to break down the complex structure is likely to be helpful by enhancing access to other parts of the structure. The efficacy of these soy enzymes in corn is unexpected as corn enzymes are best suited for corn substrates and soy enzymes are best suited for soy substrates. In addition, soy hulls include fiber of their own that are easily accessible to cellulase enzymes for conversion to glucose. The fiber-sourced glucose converted to ethanol by the fermentation organism can be calculated relative to the glucose from starch converted to ethanol. Also contemplated herein is the addition of an exogenous source of cellulase enzyme to fermentations including levels of 0.1%-10% soy flour to further increase the percentage of ethanol obtained from fiber.

Addition of soy feedstock in a small amount relative to the total feedstock (e.g. less than or equal to about 10% w/w) is beneficial in providing two sources of nitrogen for use by the yeast in propagation and fermentation. First, proteases break down protein in corn and soy into amino acids as measured by free amino nitrogen (FAN). These amino acids stimulate yeast growth and proliferation and improve fermentation efficacy. Second, ureases present in the soy convert urea to ammonia (nitrogen) used by the yeast.

The ammonia also increases the pH of the fermentation, providing benefits to yeasts, e.g. Consolidated Bioprocessing (CBP), that require a higher pH for optimum fermentation and enzyme expression. Filling a corn fermenter at a low pH, for example, about pH 4.0 to about pH 4.3, and adding soy flour and urea later in fermentation permits the ability to increase pH later in fermentation. The low starting pH can inhibit bacteria at the beginning of fermentation, and the rise in pH contributes to optimum yeast health as fermentation continues.

The addition of small amounts of urea and urease, e.g. soy flour, to corn feedstock during propagation, as disclosed herein, provides a nutritional benefit for the yeast resulting in higher yeast counts, larger yeast cell size, and improved viability. Fermentations inoculated from these yeast propagations show improved fermentation efficiency including improved kinetics and increased ethanol production. The benefit of including urea and urease in propagation can be further enhanced by the addition of exogenous enzymes along with soy flour. These exogenous enzymes can include additional enzymes, e.g., protease, lipase, phytase, pectinase, and cellulase.

Addition of soy to the feedstock can directly contribute essential amino acids that complement the amino acid content of corn and enhance the nutrient profile of the DDG. Important amino acids including lysine, methionine, phenylalanine, valine, threonine, tryptophan, leucine, isoleucine, and histidine can be enhanced in the DDG from about 5% to about 25%. Lysine, for example, can be found in amounts of at least about 25% higher in the DDG relative to DDG from corn starch fermentations in the absence of soy flour.

Use of urease, either as a reagent or urease containing feedstock, e.g. soy, in combination with urea boosts protein content while minimizing non-protein nitrogen (NPN) in animal feed coproducts or yeast-based feed ingredients (e.g., probiotic pastes). The conversion of urea to ammonia is a simple and safer way of adding nitrogen for yeast health and/or protein enhancement of ethanol coproduct streams. Ammonia can be metabolized by the yeast and is more useful to microbes than urea. Yeast numbers and viability increase and yeast size increases.

Total DDG protein, in addition to essential and complementary amino acids mentioned above, can be increased by including soy feedstock in a small amount relative to the total feedstock (e.g. less than or equal to about 10% w/w). Dehulled, full fat soy flour is about 46 to about 47% protein and is also very low in fiber due to dehulling. Supplementation of corn feedstock with 5% dehulled full-fat soy flour in fermentation can increase the DDG protein content by about 25% on a relative protein basis.

Inclusion of soybean in feedstock can increase oil for oil recovery and for maintenance of fat content in DDG. Dehulled, full fat soy flour is 22% oil, while corn is about 4% oil. In some aspects, the soybeans can be high oleic acid soy beans, providing a particular fat profile for the extracted oil or the DDG oil. Depending on the desired level of oil extraction, the protein and essential amino acid content can be enhanced further than the values indicated above, as removal of oil concentrates profiles of the other components.

In some aspects, lipoxygenase present in soybean can provide a whitening or bleaching effect, providing a lighter, whiter DDG.

In some aspects, soybean is included in the fermentation to reduce antibiotic use in animal feeding operations. Natural phytochemicals in soybeans have numerous bioactivities in biological systems and have strong antibacterial activity against various bacteria, including antibiotic resistant bacteria. By maintaining enzyme active soy containing phytochemicals in propagation and fermentation, the antibacterial activity of the resulting DDG can be increased. Exemplary phytochemicals found in soy include soy genistein, soybean isoflavone, soy daidzein, saponins, and beta-sitosterol.

Compositions

The disclosure encompasses compositions comprising a primary feedstock, urease, urea, a microorganism, and water. The urease can be in reagent form or can be endogenous to urease containing feedstock or can be produced by a microorganism. Suitable urease containing feedstocks include seeds and or derivatives from soybean (e.g. *Glycine max*), jack bean (e.g. *Canavalia ensiformis*) and/or winged bean (e.g. *Psophocarpus tetragonolobus*). The primary feedstock can comprise about 90.00% to about 100.00% w/w sugar or sugar polymer containing material, e.g. milled corn grain, and about 0.00% to about 10.00% w/w urease containing feedstock, for example, an amount less than or equal to about 10% w/w, or from about 0.05% w/w to about 10.00% w/w of the total feedstock, for example, about 2% or about 2.5% w/w to about 7.5% or about 8% w/w, or about 5% w/w, or about 5% or about 7.5% w/w to about 10% w/w, of the total feedstock. Aspects where the primary feedstock comprises about 100.00% w/w sugar or sugar polymer containing material include those in which the urease is added to the composition as a reagent rather than as endogenous to feedstock.

The microorganism can be a yeast or bacteria, genetically modified or non-GMO. An exemplary GMO useful in the methods and compositions described herein is one engineered to produce urease.

Such compositions can further comprise one or more of a cellulase, lipase, protease, and phytase.

The disclosure also encompasses compositions comprising DDG. The DDG can exhibit: (a) higher protein content; (b) improved essential amino acid profile; (c) decreased pigmentation; and/or (d) antibacterial activity, among other unexpected characteristics. The improved characteristics of the DDG are relative to the characteristics exhibited by DDG obtained from fermentation performed in the absence of soy, urease, and/or urea.

Methods

Improved microorganism health and fermentation can be achieved by adding urease to fermentation feedstock. Improving fermentation efficiency can be achieved by: (a) combining a feedstock, urease, urea, a microorganism, and water in a fermenter; and (b) fermenting the feedstock. The fermentation efficiency is improved relative to the fermentation efficiency achieved in the absence of urea and urease. As described above, urease can be in reagent form or can be endogenous to the feedstock used in propagation or fermentation.

The improved fermentation efficiency provides at least one benefit selected from the group consisting of: (a) increased ethanol production; (b) decreased residual starch; (c) increased quantity of DDG; (d) higher protein content DDG; (e) improved essential amino acid profile of DDG; (f) increased oil recovery; (g) decreased DDG pigmentation; and (h) increased fiber to ethanol conversion.

Increased oil recovery can be achieved with minimal increase in drop solids. Similarly, higher protein content DDG can be achieved without a concurrent increase in NPN.

Soy can provide an improved essential amino acid profile of DDG.

Further disclosed are methods of increasing ethanol produced from fermentation and/or increasing the rate of fermentation. The methods comprise: (a) combining urease and/or about 0.00% to about 10.00% w/w urease containing feedstock and/or a urease producing microorganism, about 90.00% to about 100.00% w/w sugar or sugar polymer containing material (e.g. milled corn grain), yeast, urea, and water in a fermenter; and (b) fermenting the feedstock to produce beer. Recovering a product, e.g. ethanol, from the beer in an amount that is increased relative to the ethanol recovered from beer produced by fermentation of corn in the absence of urease. The urease containing feedstock can be seeds or derivatives of soybeans (for example, raw, uncooked, enzyme active, de-hulled soy flour), jack bean (e.g. *Canavalia ensiformis*) and/or winged bean (e.g. *Psophocarpus tetragonolobus*). In some embodiments, the microorganism is engineered to produce urease. A perceptible increase in ethanol production is economically beneficial given the large scale production.

The urease (or urease containing feedstock or urease producing microorganism) and urea can be added during propagation, prior to fermentation, or after fermentation has been initiated. It is also contemplated that urease (or urease containing feedstock) and urea can be added at one or more timepoints during propagation and/or fermentation.

Also disclosed herein are methods of improving yeast health comprising adding urease to a fermenter or propagation tank. The urease can be added prior to milling, during milling, after milling, during propagation, and/or prior to or during fermentation.

Systems

Further provided herein are systems in which the methods and/or compositions disclosed herein are useful. In some aspects, a fermenter or propagator contains a composition as described above, e.g. a feedstock, urease, urea, a microorganism, and water. The fermenter or propagator can further contain at least one enzyme, at least one priming agent, and/or a pH adjusting agent.

In some aspects, the at least one priming agent, is a weak acid such as acetic acid at low levels.

Further provided are systems for ethanol production comprising one or more fermenters containing the compositions described herein. In some aspects, the system further comprises at least one of the following: a mill for preparation of feedstock; a propagator; and a distillation system.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided such that those of ordinary skill in the art have a complete disclosure and description of how to implement the methods disclosed herein. Efforts have been made to ensure accuracy with respect to numbers used (e.g., amounts, temperature, etc.) but some experimental errors and deviations should be accounted for. Unless indicated otherwise, parts are by weight, molecular weight is average molecular weight, temperature is in degrees Centigrade, and pressure is at or near atmospheric.

Example 1

POET's BPX™ fermentation process is a simultaneous saccharification and fermentation (SSF) process in which starch-based feedstocks such as corn are used for the production of ethanol. In this process, raw starch hydrolyzing enzymes break down the starch into monomeric glucose, which is then metabolized by the microorganism (e.g. yeast, *Saccharomyces cerevisiae*) to produce ethanol. This process may also be termed as raw starch hydrolysis or no cook process.

In this experiment, lab scale BPX fermentation was carried out. Corn (with or without soy) that was ground using a hammer mill was mixed with water to form a slurry. The slurry was prepared by weighing out the appropriate amount of corn (or corn/enzyme active de-hulled full fat soy flour soy) and water into each individual reactor. Corn solids were kept constant such that the amount of starch in each fermenter was the same. Soy flour was included at 2.5%, 5%, or 10%. Fifty percent urea was added to the fermenter at a dose equivalent to four hundred eighty-three gallons in a 550,000 gallon fermenter, a commercially representative dose appropriate for fermenters containing 30-40% solids.

A raw starch hydrolyzing enzyme blend was added and then the appropriate amount of yeast was added to the reactors, mixed well, and the reactors were placed in a circulating water bath.

Samples were withdrawn at each time point and centrifuged. The supernatant was then filtered and loaded into an auto-sampler for injection onto a reverse phase column. Aqueous sulfuric acid was used as the mobile phase (eluent). The HPLC system was fitted with a refractive index detector. Ethanol, carbohydrates (xylose, glucose, DP4+, DP3, DP2), and organic acids were identified and quantified.

The results of the experiment are illustrated in the graph shown in FIG. 1. In this graph, the percent change in ethanol production relative to the same procedure in the absence of soy is shown on the y-axis, over time, which is shown on the x-axis. The ethanol titers at initial timepoints of the fermentations indicate a faster fermentation rate using soy in corn fermentations. The data also show an overall increase in ethanol production when the fermentation was performed in the presence of soy. For example, the 2.5% soy inclusion results in an approximate 6% increase in ethanol titer over fermentation without soy at 24 hours.

Example 2

Figure 2:
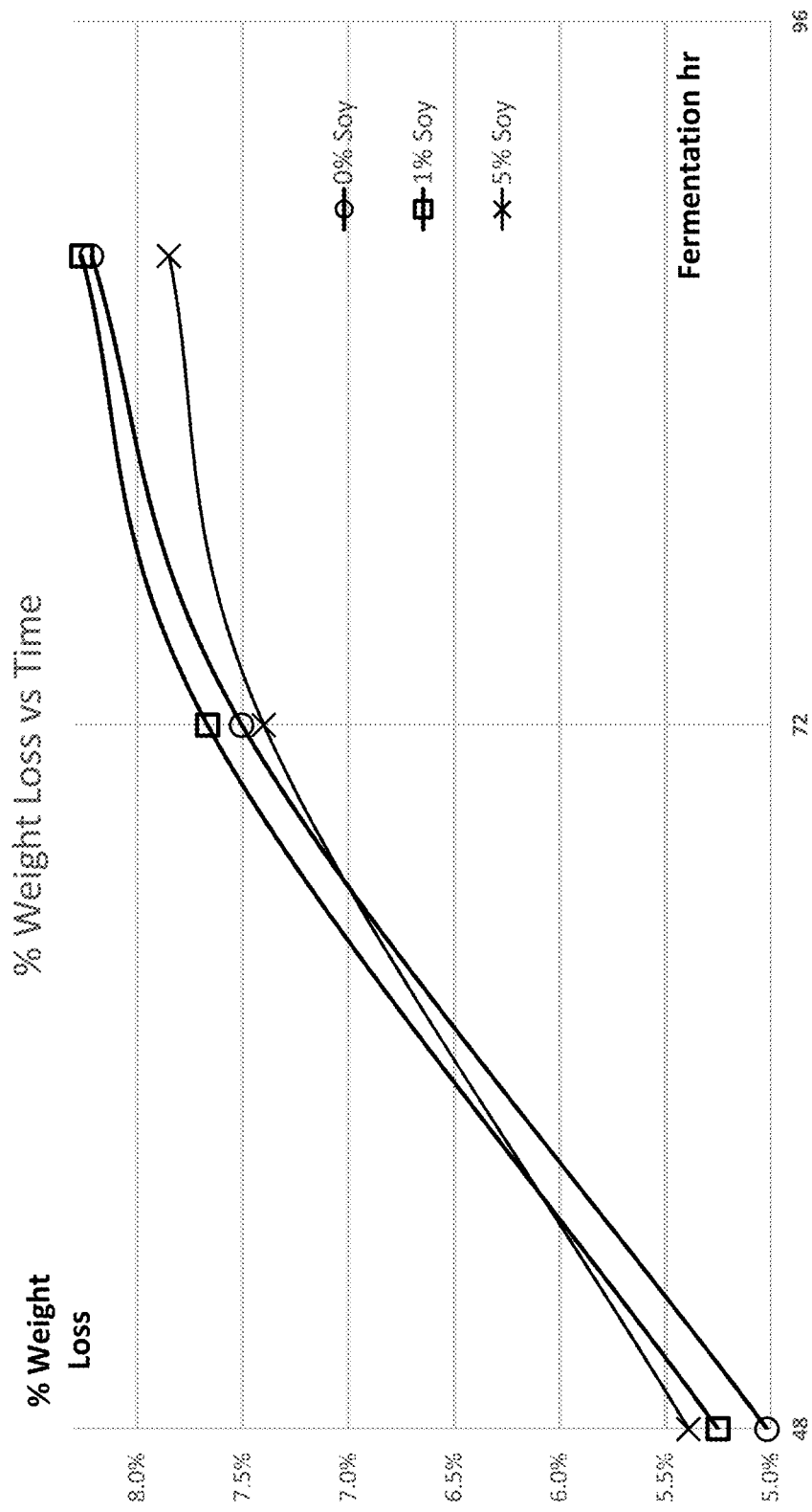
FIG. 2 shows evidence of faster kinetics of using soy flour adjuncts in corn fermentation. In contrast to the experiment used to generate the data in FIG. 1, soy was added into total solids such that fermenters with higher levels of soy had less starch. Higher weight loss is evidence of ethanol conversion during fermentation as glucose is converted to ethanol and carbon dioxide.

This experiment used the same protocol described in Example 1, except total solids were kept constant. Added soy (1% and 5%) replaced corn solids such that fermenters with higher levels of soy flour contained less starch. The graph in FIG. 2 shows percent weight loss at 48 hours, 72 hours, and 88 hours fermentation, an indicator of ethanol production. At 48 hours, inclusion of soy demonstrated higher percent weight loss relative to a corn-only fermentation which indicates an increased rate of starch conversion. The percent weight loss at 88 hours is lower relative to the zero percent soy control because the higher soy inclusion samples ran out of starch and depleted available starch more quickly.

Example 3

A slurry of ground corn with 4% soy in buffer was incubated for 24 hours at 45° C. with urea at three different concentrations. The experiment was performed at two different starting pHs (pH 4.3 and pH 4.8), and the change in pH due to conversion of urea to ammonia and carbon dioxide was measured.

Figure 3:
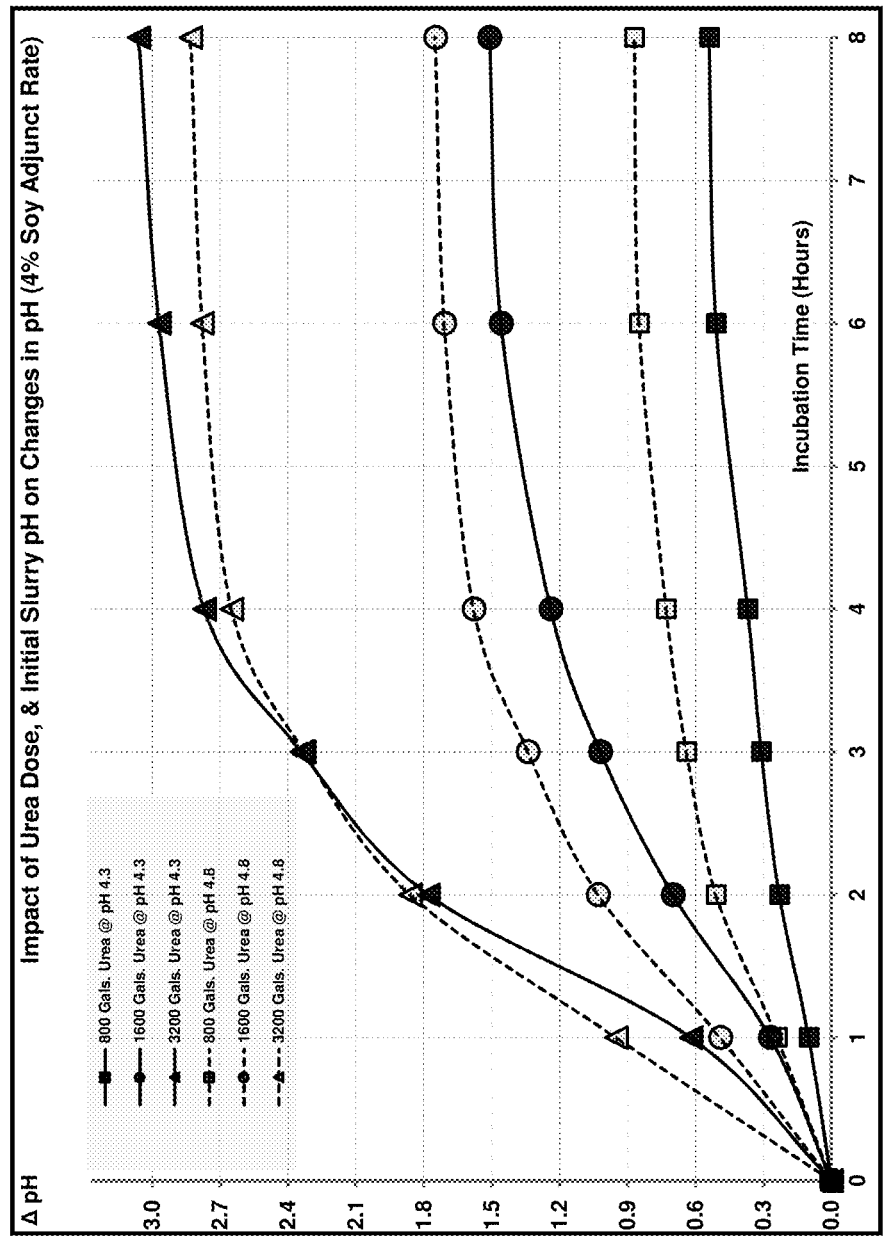
FIG. 3 depicts the pH increase upon conversion of urea to ammonia and carbon dioxide, i.e. shows the relationship between urea and pH, with 4% de-hulled enzyme active full fat soy flour added to the fermentation. This graph shows different levels of urea at two starting pH levels. Higher starting pH contributes to greater increase in pH. Higher urea addition results in higher pH due to greater amount of urea available for conversion to ammonia.

FIG. 3 shows the relationship between urea in the presence of soy flour and pH, where a higher concentration of urea at both starting pHs produced a greater change in pH. In addition, a higher starting pH generated a higher increase (delta) in pH relative to the lower starting pH. While the deltas may appear small, boosting pH by, for example, 0.3, can be the difference between a stalled fermentation and an active fermentation.

Figure 4:
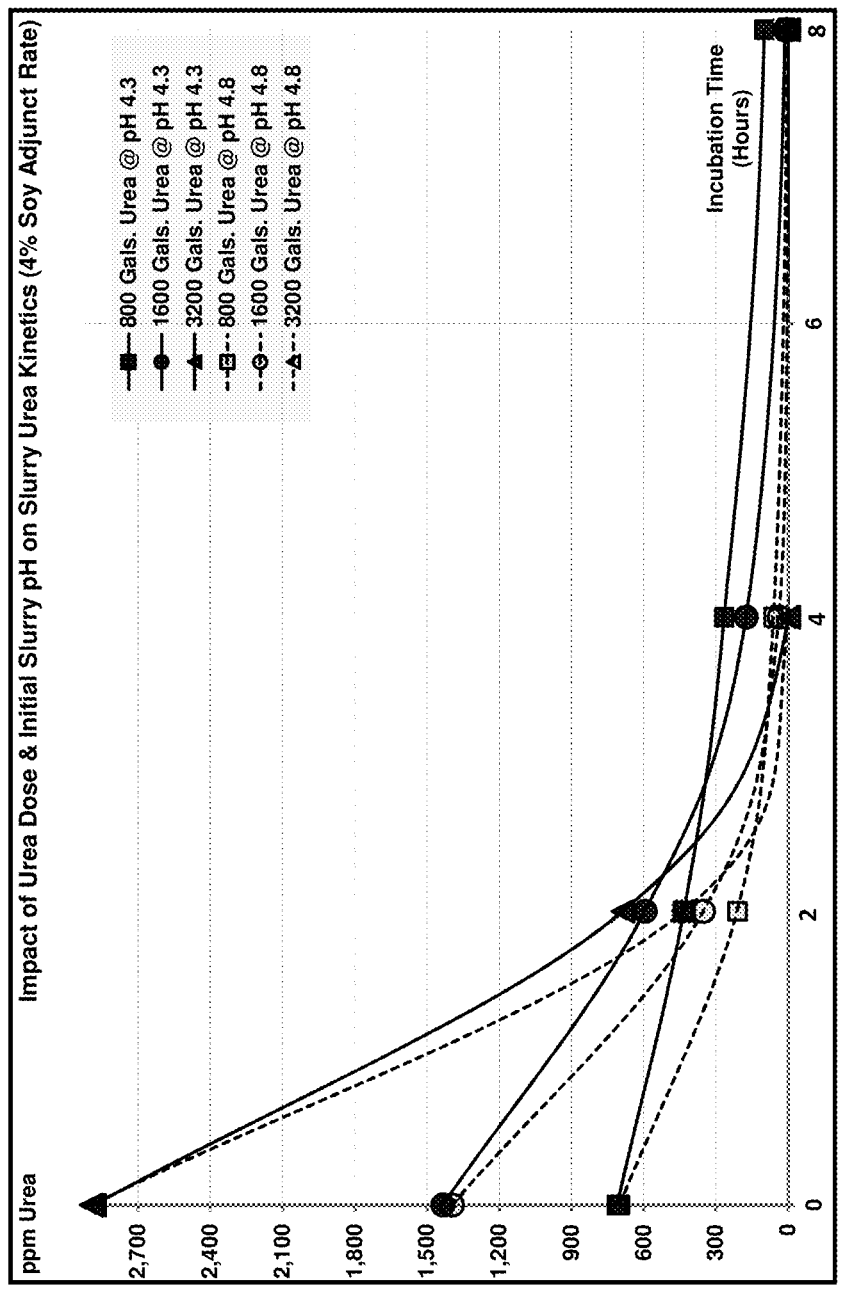
FIG. 4 also depicts the relationship between urea and pH, but in this figure the decrease in urea is shown. The graph shows that added urea can be removed quickly using soy urease.

FIG. 4 demonstrates that the added urea was converted to ammonia and carbon dioxide quickly by urease present in the soy.

Figure 5:
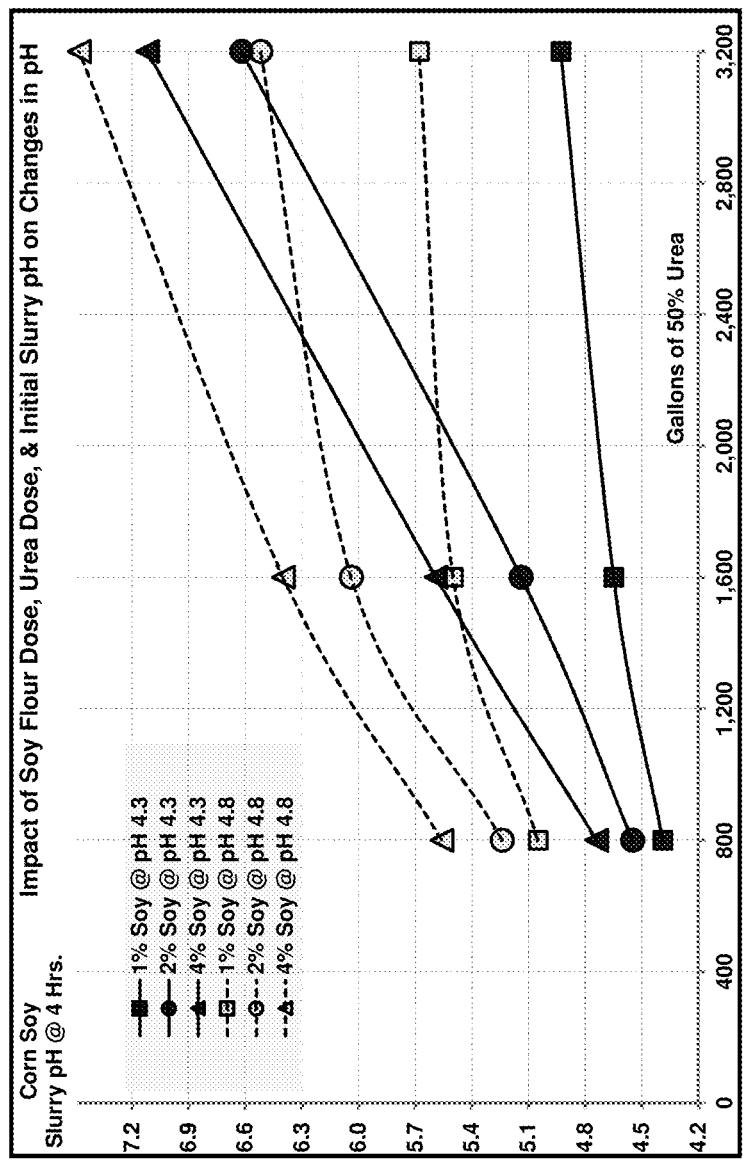
FIG. 5 shows the relationship between the amount of soy, pH, and urea dose at a snapshot during the experiment (4 hours). Even low levels of soy inclusion can be used to raise the pH.

FIG. 5 shows the relationship between the amount of soy, pH, and urea dose. The data demonstrates that, at 4 hours, even low levels of soy inclusion in the presence of urea can raise the pH.

Ammonia is a preferred nitrogen source for yeast. New strains of Consolidated BioProcessing (CBP) yeast need higher levels of nitrogen as well as higher pH than previous commodity (non GMO) yeast strains. As the added urease (whether in reagent form or endogenous to feedstock) converts the urea to ammonia, the propagation and fermentation environments can be improved without generating non-protein nitrogens in DDG from added urea.

Example 4

Figure 6:
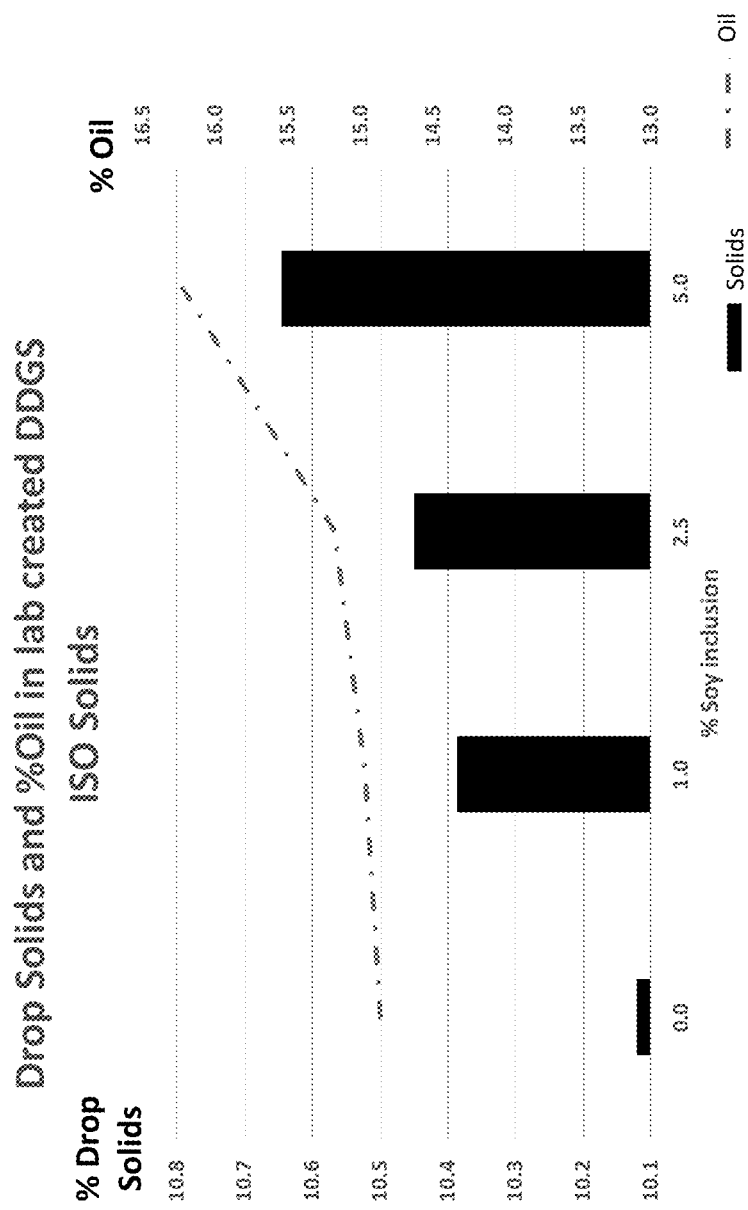
FIG. 6 and FIG. 7 show that adding soy into fermentations would increase throughput of DDG as indicated by drop solids even though total solids is held constant (isosolids). Higher drop solids indicate higher levels of solids left to make up feed product. Soy is higher in protein than corn, and protein will concentrate up in fermentation. Oil concentration in the end feed product is increased, see FIG. 6, as is protein concentration in the end feed product, see FIG. 7.

Fermentations were set up as described in Example 1, and soy replaced corn in the fermenters at 0%, 1.0%, 2.5%, or 5%. After fermentation, DDG samples were analyzed for percent drop solids and percent oil. Higher drop solids levels indicate increased DDG production. The data provided in FIG. 6 show that increasing levels of soy results in an increase in both drop solids and oil in the DDG. Soy is about 20% oil, while corn is about 4% oil.

Example 5

Figure 7:
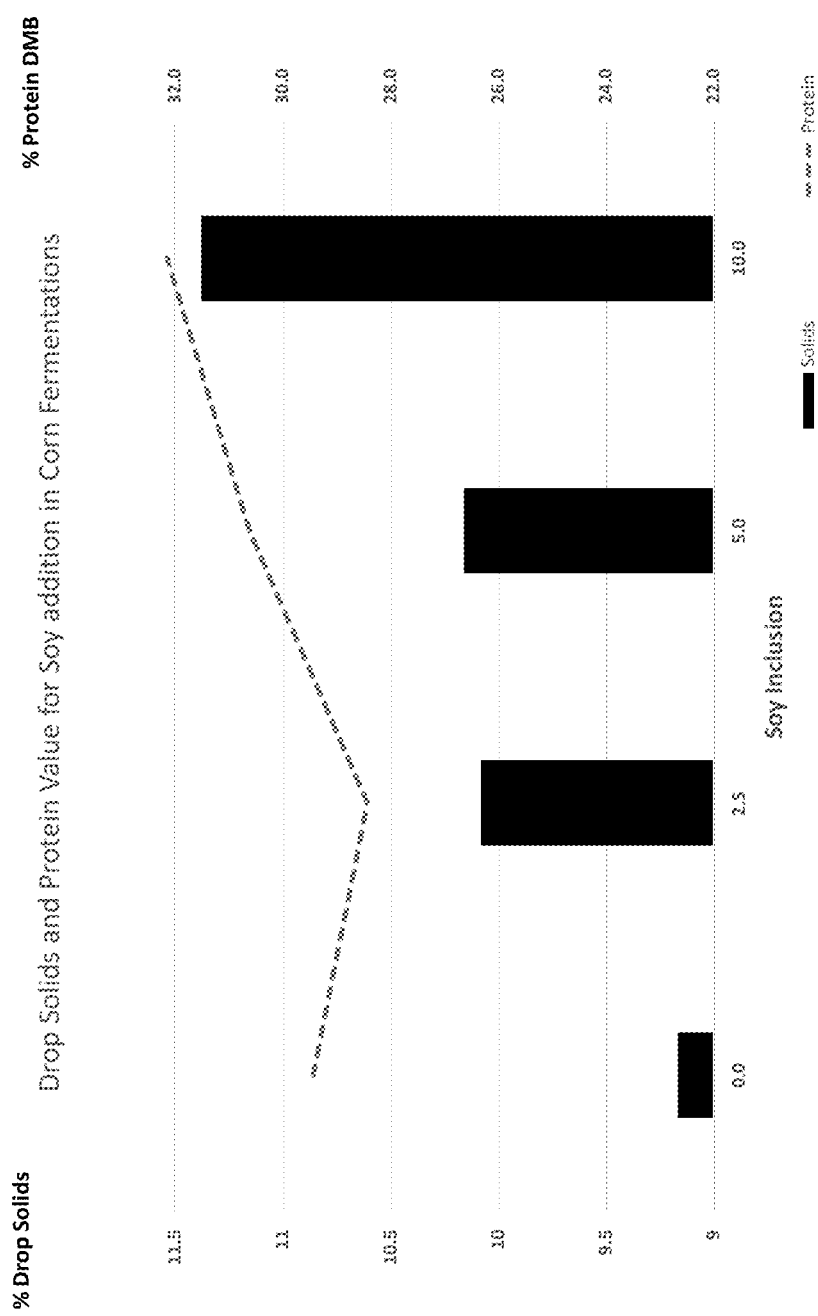

Fermentations were set up as described in Example 1, and soy replaced corn in the fermenters at 0%, 2.5%, 5%, or 10%. After fermentation, DDG samples were analyzed for percent drop solids and percent protein on a dry matter basis. Higher drop solids levels indicate increased DDG production. Soy is higher in protein than corn, and the data provided in FIG. 7 show that increasing levels of soy result in an increase in both drop solids, confirming the results shown in Example 4, and protein in the DDG. Soy is about 40% protein; corn is about 8% protein.

Example 6

Figure 8:
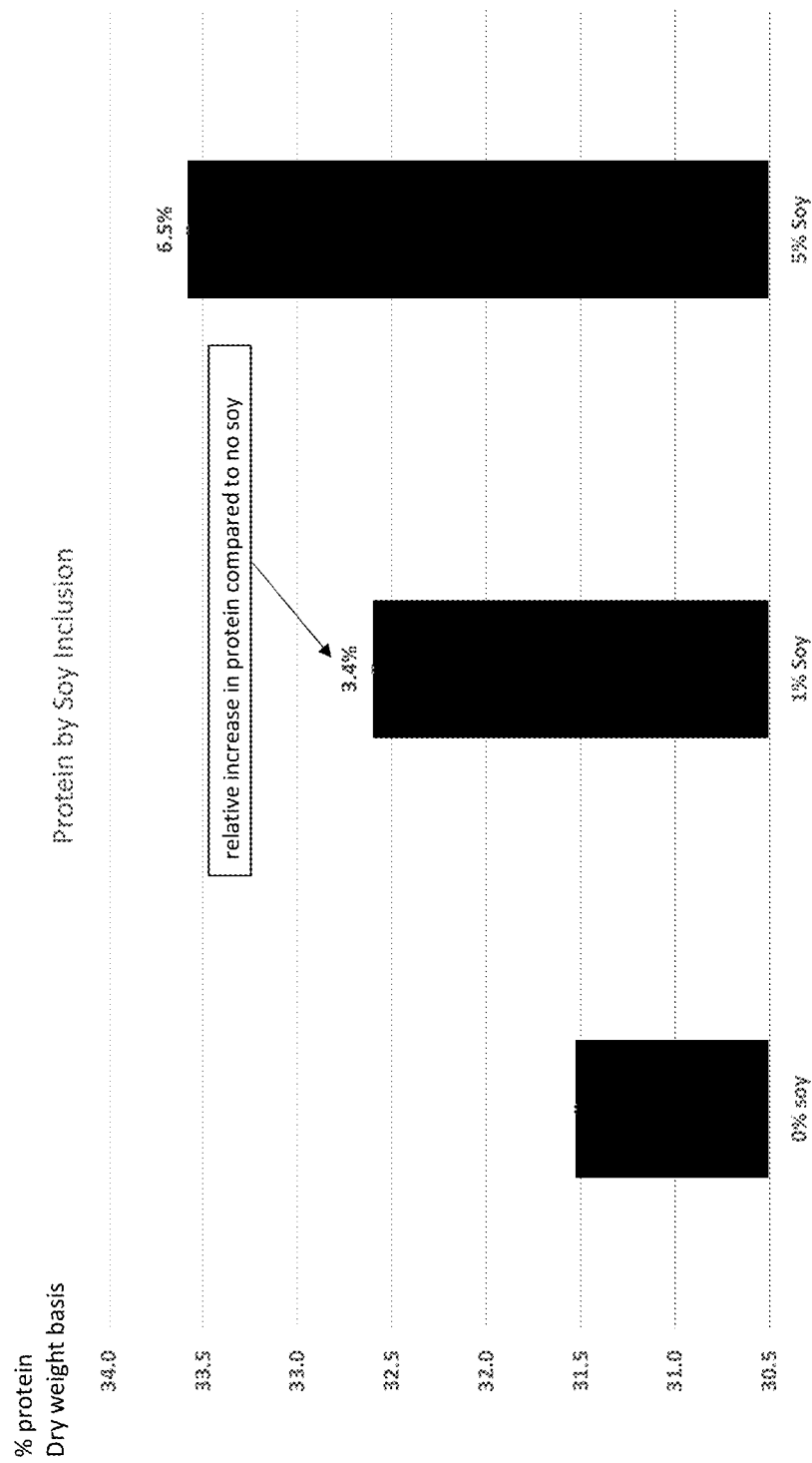
FIG. 8 shows that adding soy as an adjunct provides more protein for the final DDG product. The experiment was performed in a laboratory, but when performed in a biorefinery, 60% of the available oil is extracted and sold as a corn oil product. The same experiment performed in a biorefinery where the oil was extracted would generate much higher protein numbers.

This experiment was carried out as described in Example 2, where fermentations were performed on corn feedstock supplemented with 1% or 5% soy and the final DDG product was assayed for changes in protein content, fat content, and fiber conversion. FIG. 8 shows that 1% soy boosted DDG protein content by 3.4% and 5% soy by 6.5%. DDG with higher protein contents are more valuable as livestock feed. Of note, about 60% of the oil available is typically extracted from the DDG and sold as a corn oil product. If the oil had been extracted from the DDG prior to sampling in this experiment, the protein levels (% protein on dry weight basis, as shown on the y-axis of FIG. 8) would have been much higher.

Figure 11:
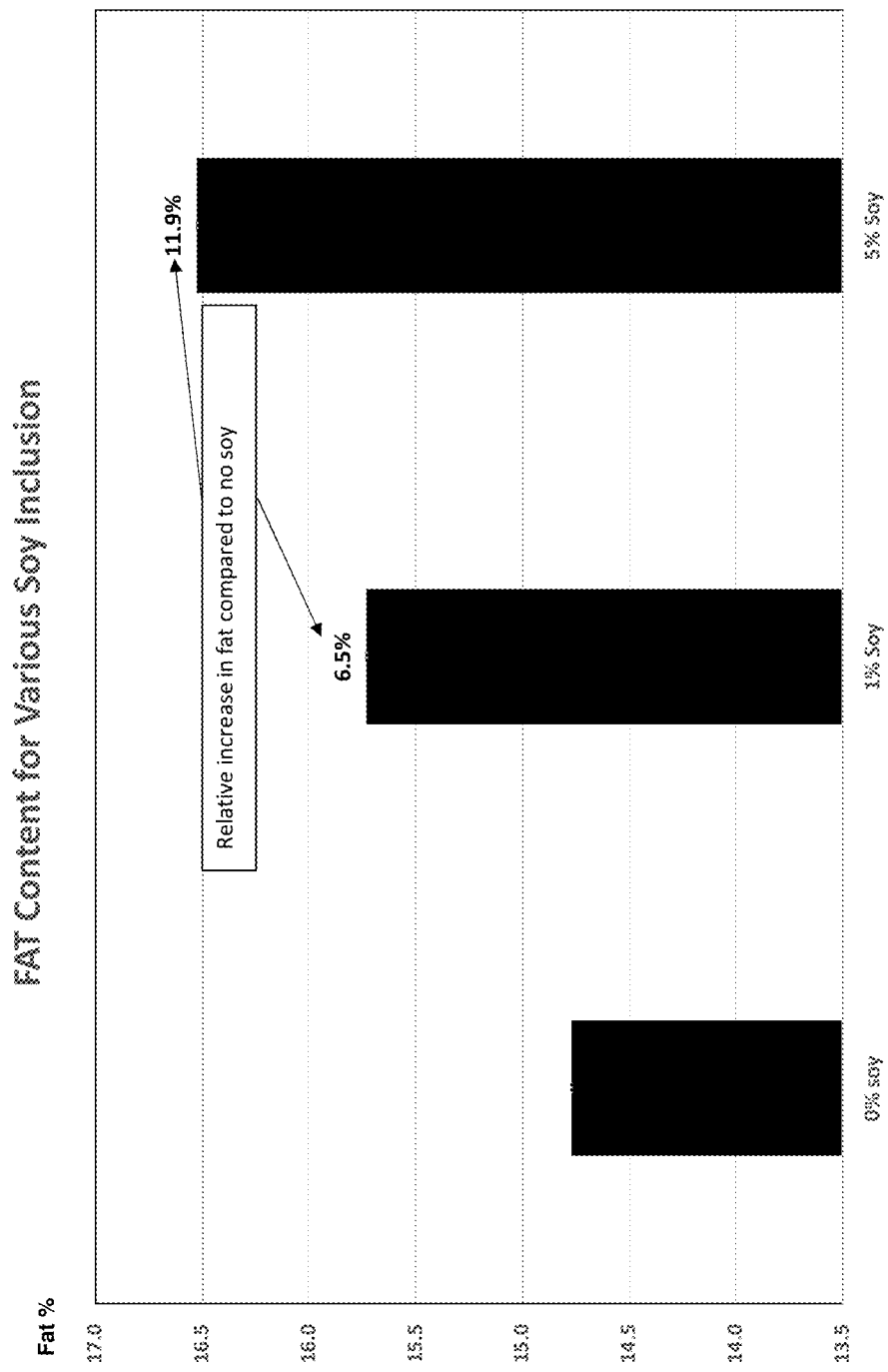
FIG. 11 also demonstrates the crude protein content of corn versus soy/de-hulled soy flour, showing the much higher crude protein content of soy compared to corn.

The graph in FIG. 11 shows that inclusion of soy in the fermentation increases DDG fat available for extraction.

Soy also impacted the fiber conversion efficiency, measured in percent of total gallons of ethanol coming from fiber, data not shown. This is surprising as corn enzymes are particularly suited for breaking down corn fiber, so it was unexpected that the soy enzymes would have much added effect on corn fibers for fermentation.

Example 7

Figure 9:
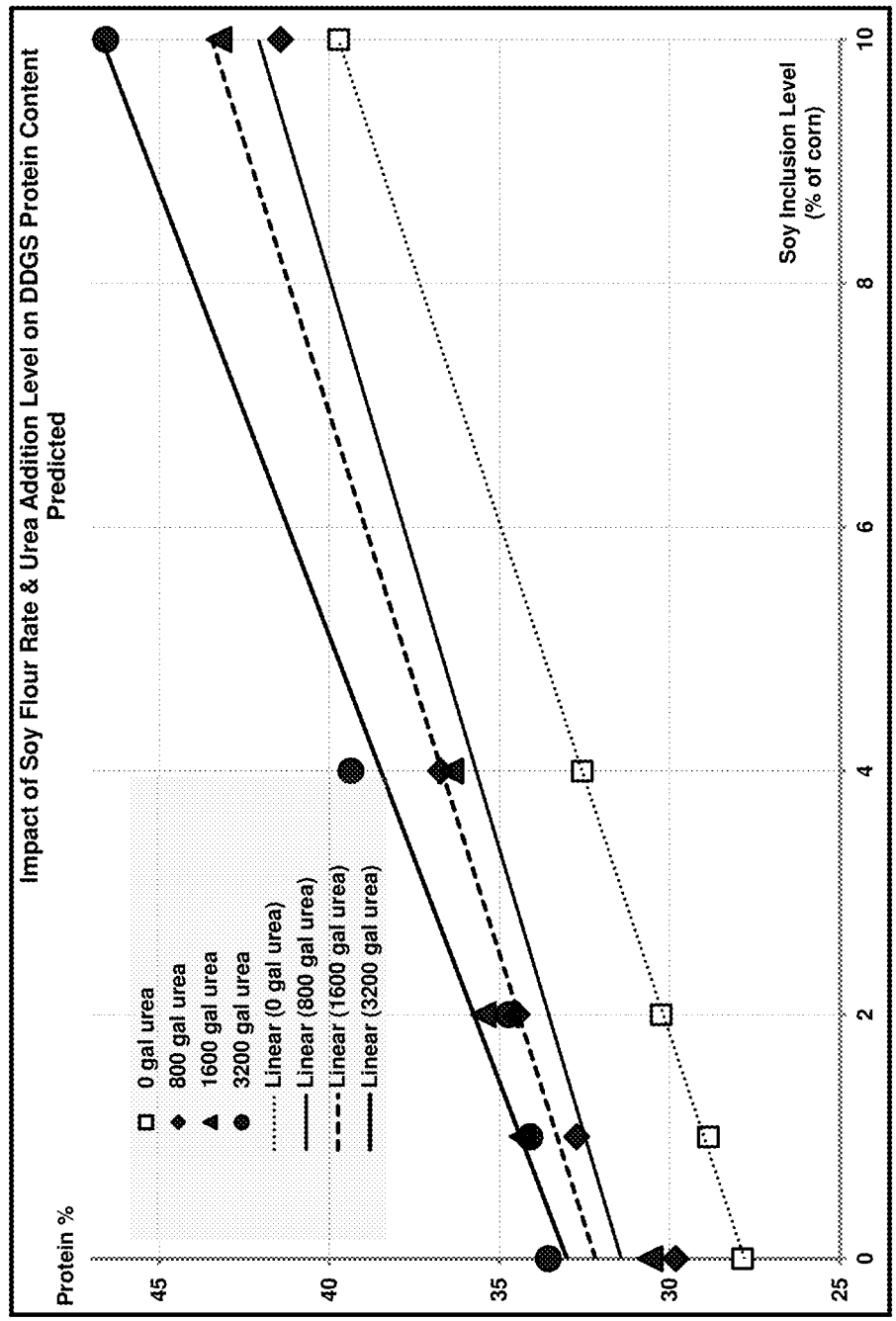
FIG. 9 depicts predicted protein content of DDG based on protein content measured in original corn/soy blends. At 10% soy flour inclusion and 3200 gallons urea in a 550,000 gallon fermenter (3320 ppm soy) the protein content increases by more than 10% relative to 3200 gallons urea in the absence of soy. Protein content of DDG is based on a 3.2× concentration of protein, a factor generally recognized as a predictor of protein in post fermentation product.

Fermentation was carried out as described in Example 1. Soy was included in the feedstock at varying percentages, in the presence or absence of added urea. Protein content in the original corn/soy blends was measured, then the predicted protein content of DDG was calculated based on a 3.2× concentration of protein (generally recognized as a predictor of protein in post fermentation product). See FIG. 9. As soy inclusion levels rise, predicted protein levels also rise but are higher than what was added. This experiment also shows the impact of adding soy or urea alone.

Example 8

Figure 12:
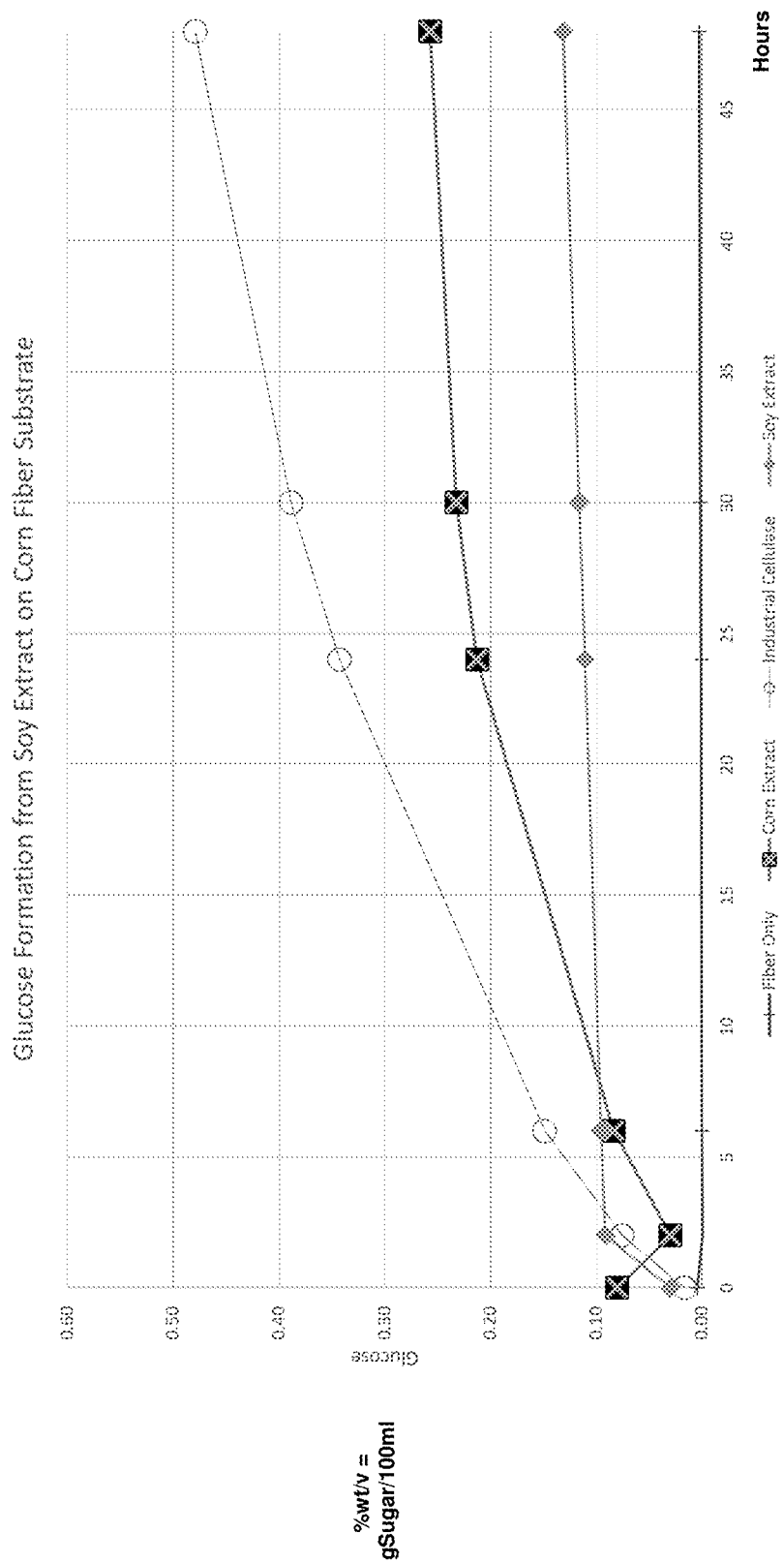
FIG. 12 shows glucose production from corn fiber substrate in the presence of soy extract. The soy extract was generated by placing soy flour in an acetate buffer at 50 mM and pH 4.5 to release enzymes that facilitate fiber availability and/or conversion. Corn fiber substrate was steeped in corn extract, soy extract, or industrial cellulase, and fiber conversion was measured by glucose formation.

Using an extract of soy flour in an acetate buffer 50 mM pH 4.5, endogenous enzymes were extracted and placed on various compositions including corn fiber substrate to demonstrate glucose production by the various endogenous soy enzymes. After a 48 hour steep at 45° C., glucose is produced showing evidence of soy enzymes breaking down corn fiber into glucose. The compositions included buffer solution only (control), corn extract in buffer (endogenous corn enzymes), industrial cellulase in buffer, and soy extract and buffer (endogenous soy enzymes). Corn contains endogenous cellulases which were expected to be more highly optimized to break down corn fiber. However, as shown in FIG. 12, after a steep of 6 hours soy enzymes were breaking down corn fiber and glucose levels were rising more dramatically compared to the endogenous corn enzymes.

Figure 13:
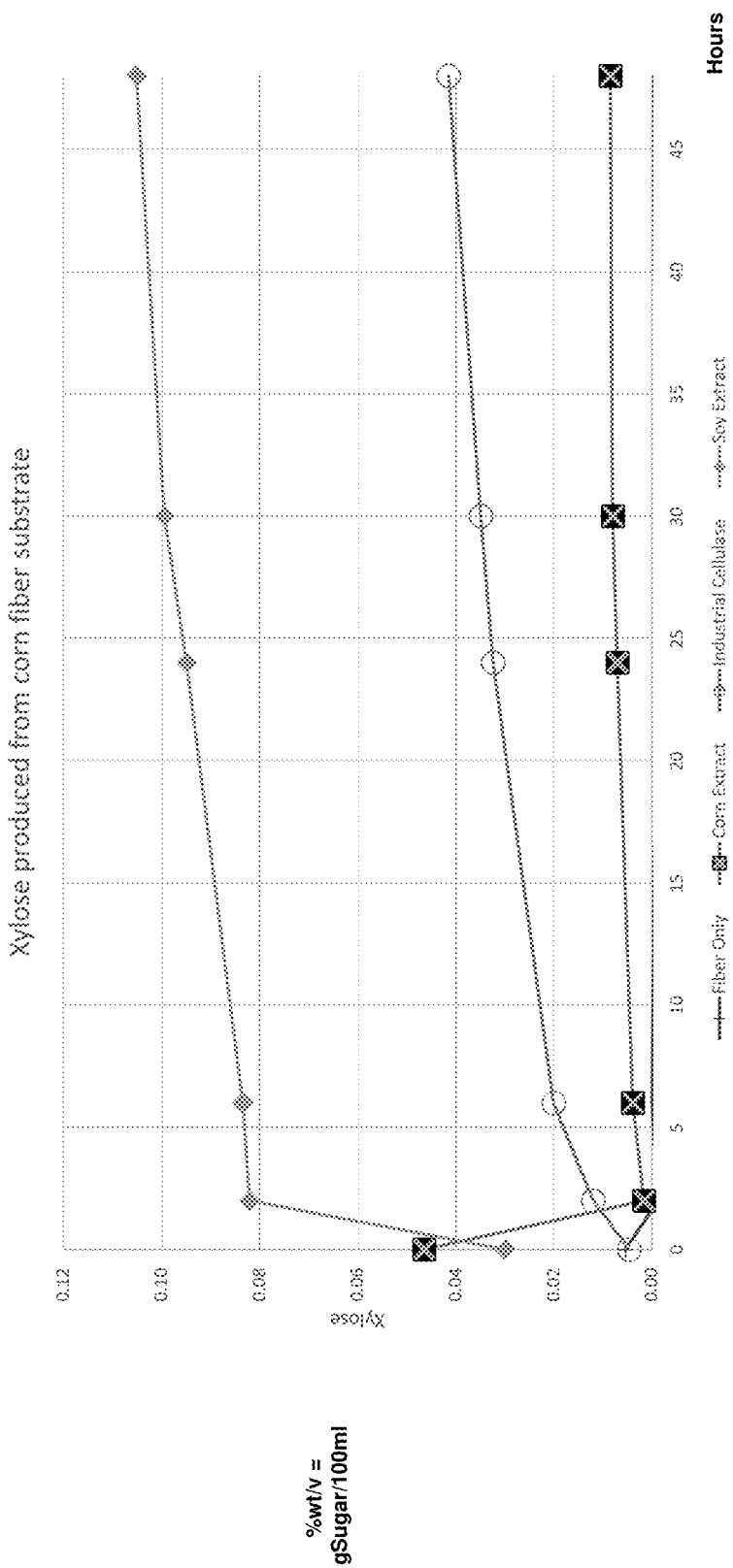
FIG. 13 shows xylose production from corn fiber substrate in the presence of soy extract. Corn fiber substrate was steeped in corn extract, soy extract, or industrial cellulase, and fiber conversion was measured by xylose formation. Surprisingly, enzymes in soy facilitate the breakdown of corn fiber.

Similarly, FIG. 13 shows xylose production from corn fiber substrate by soy enzymes in comparison to corn enzymes and in comparison to industrial cellulase. Xylose is evidence of structural breakdown of the corn fiber. The soy extract is more effective than the other two compositions. It may be, without being held to theory that soy extract contains higher levels of hemicellulases or other xylose liberating enzymes than corn extract. This experiment provides evidence that enzyme active soy breaks down corn fiber and in doing so exposes other substrates available for fermentation. It is also contemplated that future GMO yeast or other GMO microorganisms will have the ability to utilize xylose in fermentation.

Additional fiber conversion can be obtained from soy beans or soy hulls containing fiber (in as much as soy hulls are easily converted), enabled by the endogenous enzymes in the soy.

Example 9

Example 7 provided evidence that including soy in corn fermentations improved fiber to ethanol conversion. This experiment confirmed the findings of Example 7. In this experiment a lab fermentation performed in accordance to Example 2. Including soy in corn fermentations allows for an increase in fiber conversion into ethanol. The fiber converted fraction measurement is a calculation of total gallons produced that come from cellulose. This calculation considers the composition of the original feedstock, and the composition of the ending product. Knowing these calculations, a percent of gallons of ethanol produced coming from the fiber portion in the original feedstock can be calculated.

Figure 14:
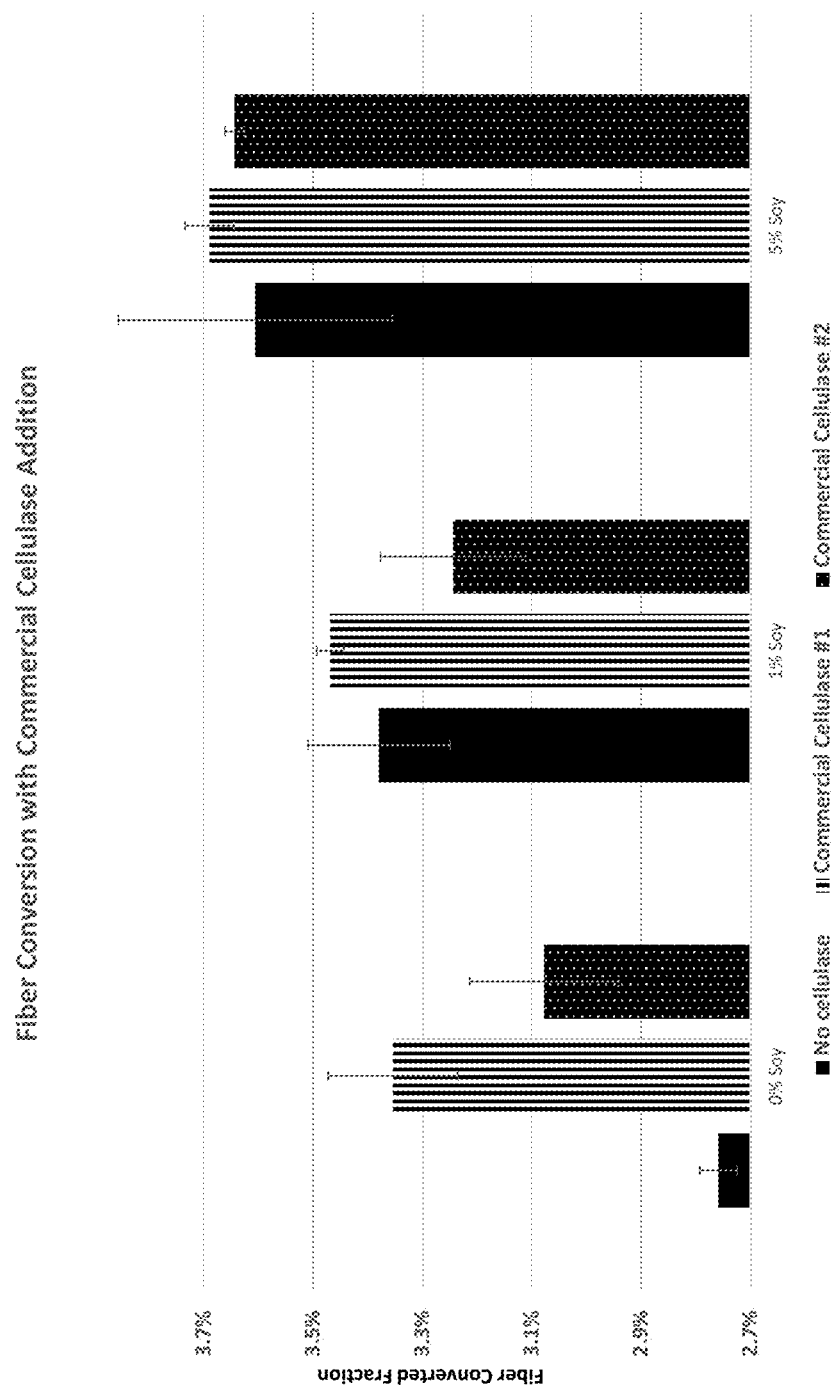
FIG. 14 shows that greater fiber to ethanol production is achieved when both soy and cellulase are added to the corn fermentation, compared to soy or cellulase alone. The data also shows that soy can replace cellulase in a corn fermentation and the percentage of gallons of ethanol produced from fiber will be comparable.

Two sources of increased fiber conversion are likely from endogenous enzymes breaking down corn fiber structure, as well as the fiber present in the soybean hull. The data confirms the findings of Example 7, while also demonstrating even further fiber conversion efficiency by including commercial cellulase. See FIG. 14.

Example 10

The Ninhydrin-Based Free Amino Nitrogen Reaction was used to determine the amount of free amino nitrogen in liquid samples to provide information regarding the quantity of amino nitrogen available to yeast during fermentation, or the quantity of amino nitrogen remaining in the beer after fermentation. The method measures amino acids, ammonia, and to some extent, end group α-amino nitrogen in peptides and proteins. Proline is not measured to any extent at the wavelength used. The method is not specific for α-amino nitrogen since γ-amino butyric acid, which is present in both mash and beer, yields substantial color with ninhydrin (The American Society of Brewing Chemists).

In this experiment, fermentations were performed using corn with varying percentages of soy as feedstock as described in Example 1. Samples were obtained after completion of fermentation and diluted. Ninhydrin color reagent was added to each sample then the samples were placed in a boiling water bath for 16 minutes. After cooling and further diluting each sample, absorbance was measured for each sample and FAN calculated according to the following formula.

$$FAN(mg/L) = sample\ absorbance/standard\ absorbance \times 6.0 \times d$$

Where d is the Dilution Factor of the sample.

Figure 15:
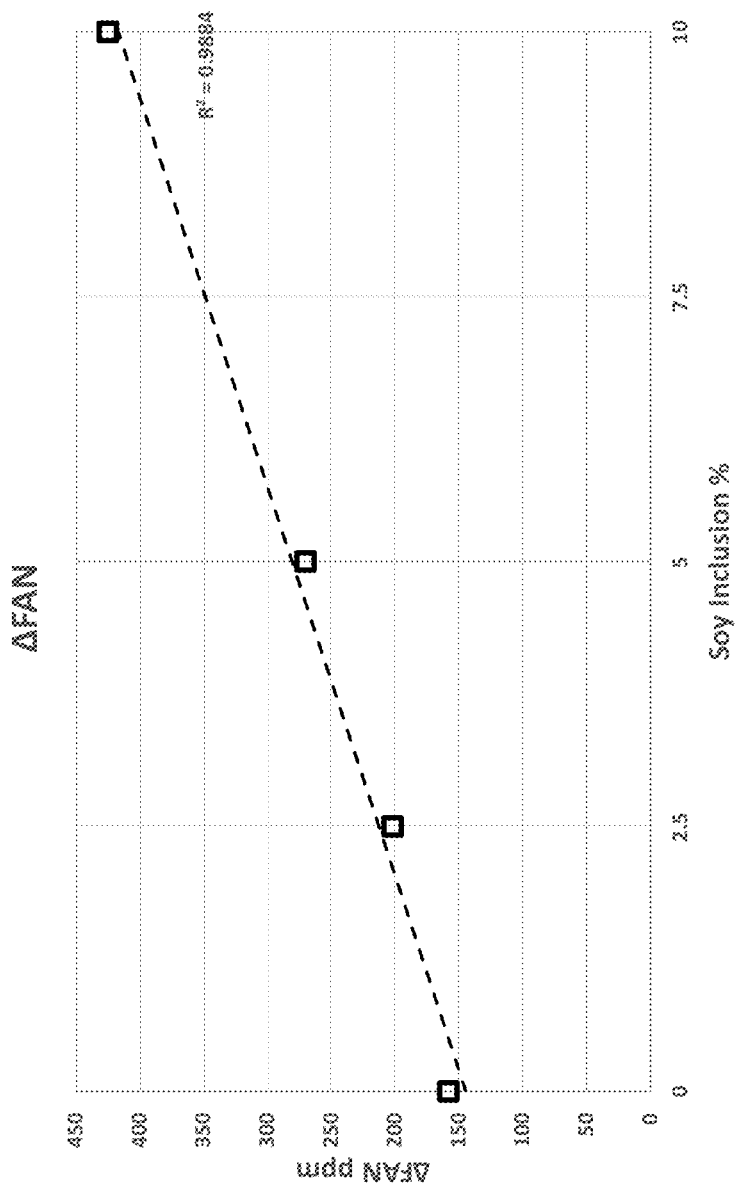
FIG. 15 depicts the relationship between soy and free amino nitrogen (FAN) and presents the data as Delta FAN, i.e. the difference between FAN measured at 0 hours and FAN measured at 24 hours. As soy in the fermentation is increased, Delta FAN levels increase (ppm).

A change in FAN indicates the action of endogenous proteases from e.g. corn and/or soy on the protein present. FIG. 15 shows an increase in delta FAN as the percentage of soy increases from 2.5% to 10%. Delta FAN is the difference between time zero FAN and FAN after 24 hours of incubation. Additional FAN stimulates yeast growth and fermentation and contributes to improved fermentation efficiency. A change in FAN indicates the action of endogenous proteases on protein present in the corn and/or soy.

Example 11

Propagation is different than fermentation in that the goal of propagation is to promote growth of yeast cells as opposed to ethanol production in fermentation. The conditions of the propagation reactor can be controlled to provide an environment conducive to cellular reproduction and yeast health. These conditions may include aeration, agitation, pH, temperature, and/or the presence of antimicrobials, additional nutrients, and/or accessory enzymes. Propagation also serves as a conditioning step for the yeast between storage of the commercial yeast preparation and the production fermenter.

Figure 16:
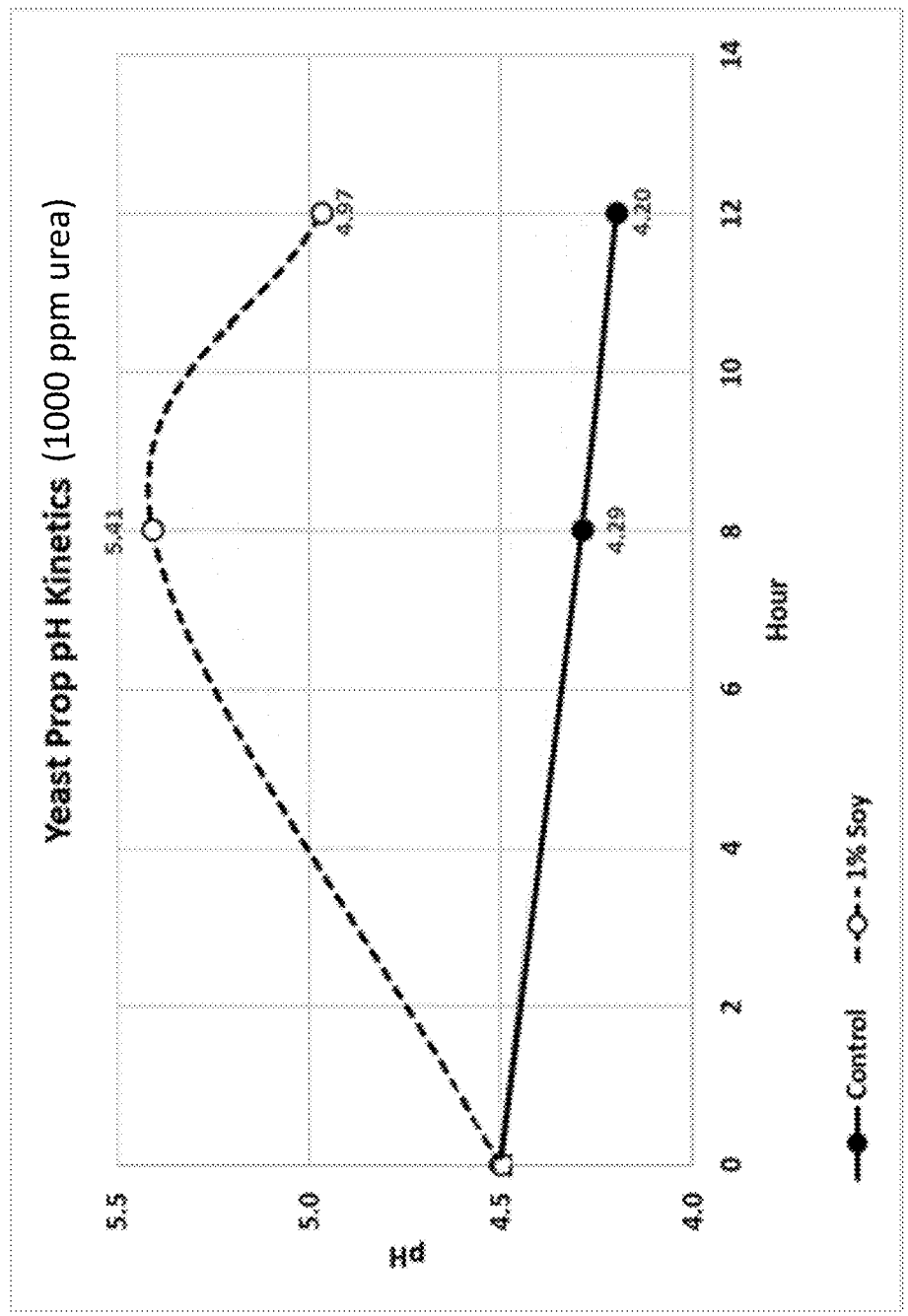
FIG. 16 shows that addition of soy and urea to propagation increases the pH of the media, providing a more ideal growth environment for yeast cells.

This experiment tested the effect of soy and urea on the pH profile and yeast growth during propagation. A slurry of ground corn and soy in water was combined with yeast and a blend of amylases in a propagation tank, along with 1000 ppm urea, and the pH adjusted to 4.5. The samples were agitated at 150 rpm and left at 30 to 32.2° C. for 12 hours. Samples were obtained at 8 and 12 hours. As can be seen in FIG. 16, the pH in tanks containing no soy dropped over time. In tanks containing soy, the pH rose to near or above 5, an optimal pH for many GMO yeast.

Figure 17:
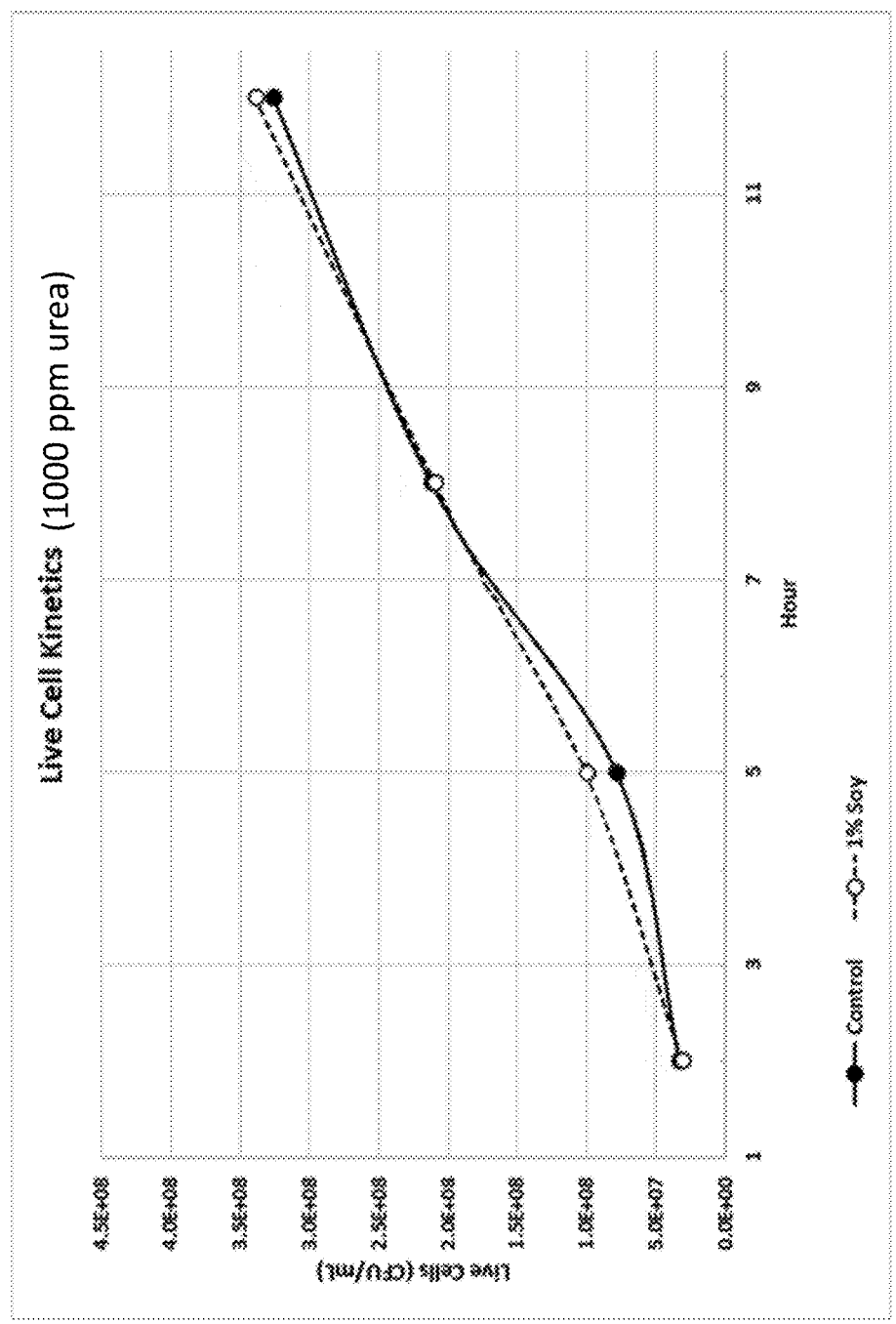
FIG. 17 shows that addition of soy to propagation along with a blend of accessory enzymes increases cell replication.

Data shown in FIG. 17 confirms that including soy in the feedstock positively impacts yeast growth.

Example 12

*Saccharomyces* yeast lack urease. Soybean urease can hydrolyze urea to ammonia and $CO_2$, providing additional amino nitrogen to stimulate yeast growth and fermentation. The urease can also provide a pH increase in fermentation, providing benefits to CBP yeasts that require a higher pH for optimum fermentation and enzyme expression. In this experiment, soy hulls were mixed with pH 4.5 buffer. One portion of the soy hulls was heat treated for 24 hours at 100° C., the other was collected from soy processing plant.

Figure 18:
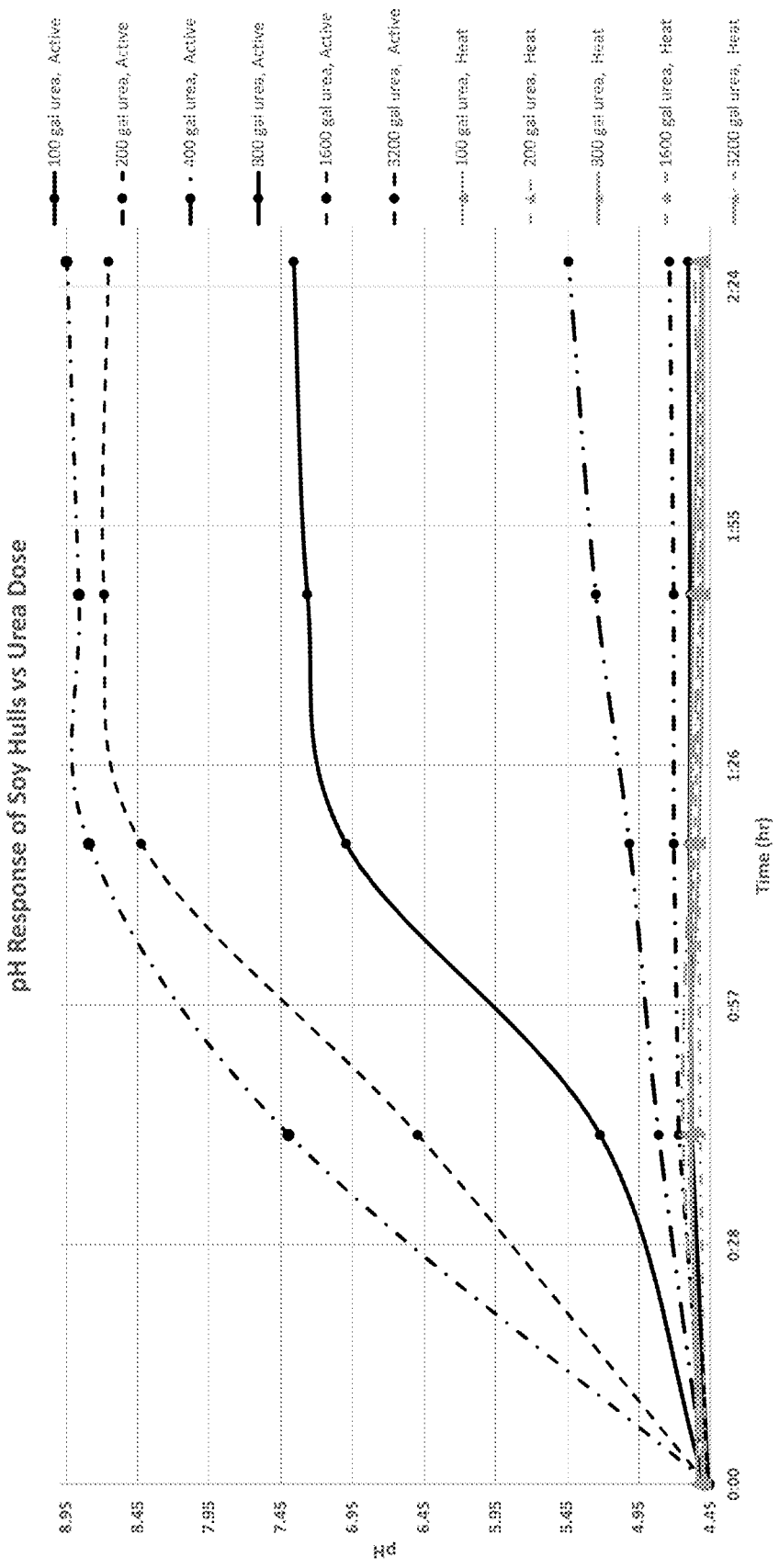
FIG. 18 shows urease activity in soy hull fraction due to increase in pH in the presence of urea for non-heat treated samples. Additionally, heat treated samples showed no pH change indicating a denaturing of the urease enzyme due to heat treatment.

Varying amounts of urea were added and the pH response of the soy hulls versus the urea dose over time is shown in FIG. 18. The data shows evidence of urease activity in the soy hull fraction due to increase in pH in the presence of urea for non-heat treated samples. In addition, heat treated samples showed no pH change indicating a denaturing of the urease enzyme due to heat treatment.

Example 13

In this experiment, soy hulls (3% or 6%) were mixed with whole stillage and the mixture was set to a starting pH of 5.5. Two different concentrations of urea were added (50% solution equivalent to 800 gallons or 1600 gallons), and the change in pH was measured over time for the four combinations.

Figure 19:
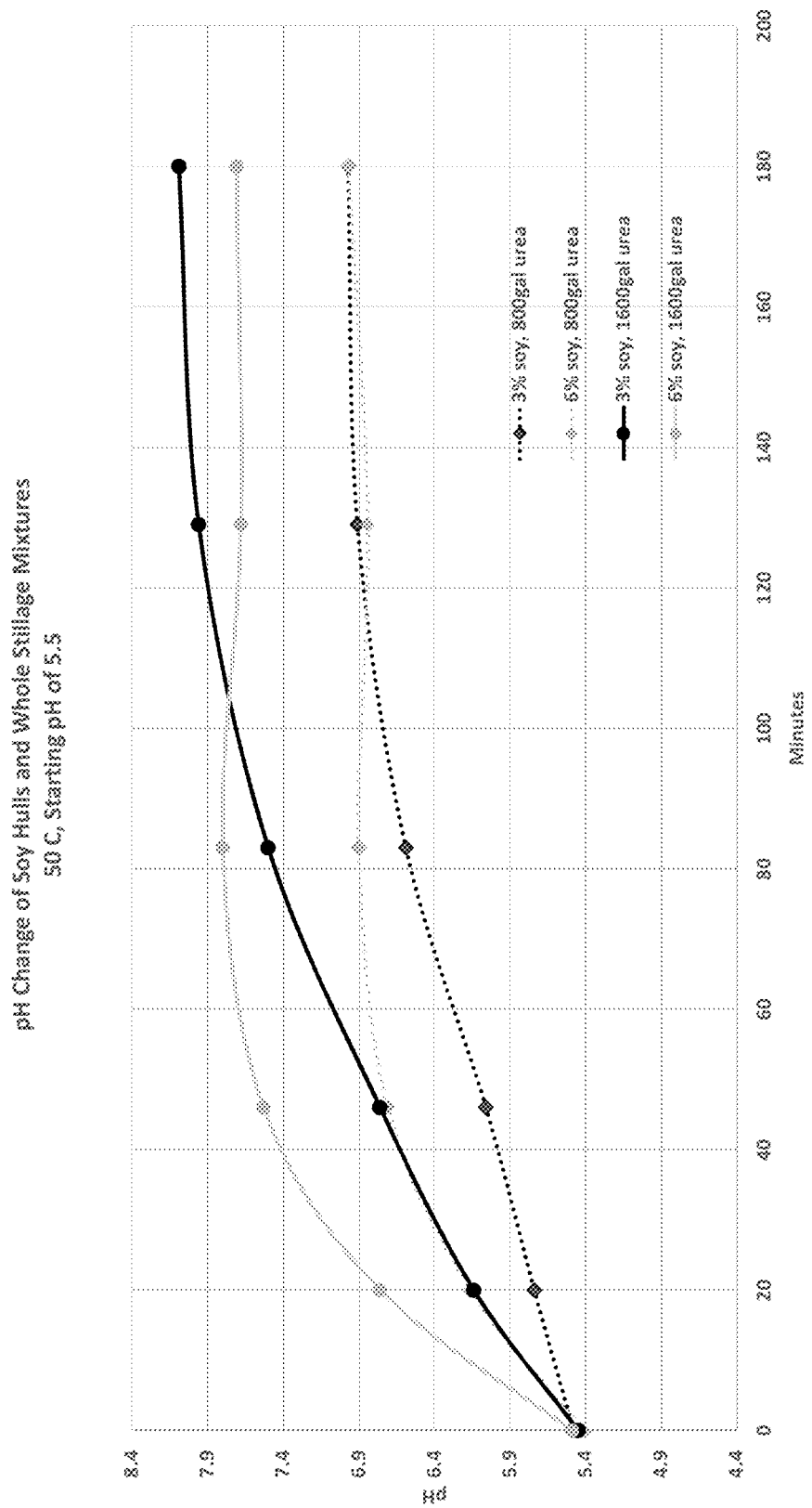
FIG. 19 demonstrates urease activity in soy hull fraction and evidence of potential high pH values achieved by including soy hulls.

FIG. 19 shows an increase in pH. The higher soy inclusion examples demonstrated a fast rate and the pH plateaued after approximately 90 minutes. The lower soy inclusion examples plateaued after approximately 130 minutes. The data provides evidence of urease activity in the soy hull fraction and demonstrates the high pH values achieved by including soy hulls.

What is claimed is:

1. A composition comprising: (a) a feedstock comprising (i) milled corn grain and (ii) enzyme active whole soybean or enzyme active de-hulled soybean, (b) urease, wherein the urease is endogenous to the soybean, (c) urea, (d) a microorganism, and (e) water, further comprising one or more of a cellulase, lipase, protease, and phytase.

2. The composition of claim 1, wherein the feedstock comprises 90.00% to 99.95% w/w milled corn grain and 0.05% to 10.00% w/w enzyme active whole soybean or enzyme active de-hulled soybean.

3. The composition of claim 1, wherein the enzyme active whole or enzyme active de-hulled soybean is enzyme active soy flour.

4. The composition of claim 1, wherein the microorganism is yeast.

5. A composition comprising: (a) a feedstock comprising (i) milled corn grain and (ii) enzyme active whole soybean or enzyme active de-hulled soybean comprising endogenous urease, (b) urea, (c) a microorganism, and (d) water; wherein the enzyme active whole soybean or enzyme active de-hulled soybean is obtained from soybean not exposed to temperatures greater than 71° C.

6. The composition of claim 5, wherein the feedstock comprises 90.00% to 99.95% w/w milled corn grain and 0.05% to 10.00% w/w enzyme active whole soybean or enzyme active de-hulled soybean.

7. The composition of claim 5, wherein the enzyme active whole or enzyme active de-hulled soybean is enzyme active soy flour.

8. The composition of claim 5, wherein the microorganism is yeast.

9. A method of improving fermentation efficiency comprising:
   (I) combining (a) a feedstock comprising (i) milled corn grain and (ii) enzyme active whole soybean or enzyme active de-hulled soybean, (b) urease, wherein the urease is endogenous to the soybean, (c) urea, (d) a microorganism, (e) one or more of a cellulase, lipase, protease, and phytase, and (f) water in a fermenter; and
   (II) fermenting the contents of the fermenter;
   wherein the fermentation efficiency is improved relative to the fermentation efficiency achieved in the absence of urea and urease.

10. The method of claim 9, wherein the improved fermentation efficiency provides at least one benefit selected from the group consisting of:
    (a) increased ethanol production;
    (b) decreased residual starch;
    (c) increased quantity of dried distillers grains (DDG);
    (d) higher protein content DDG;
    (e) improved essential amino acid profile of DDG;
    (f) increased oil recovery;
    (g) decreased DDG pigmentation; and
    (h) increased fiber conversion.

11. The method of claim 9, wherein the feedstock comprises 90.00% to 99.95% w/w milled corn grain and 0.05% to 10.00% w/w enzyme active whole soybean or enzyme active de-hulled soybean.

12. The method of claim 11, wherein the enzyme active whole soybean or enzyme active dehulled soybean is enzyme active soy flour.

13. The method of claim 11, wherein the enzyme active whole soybean or enzyme active dehulled soybean is uncooked.

14. The method of claim 9, wherein the microorganism is yeast.

15. A method of improving fermentation efficiency comprising:
    (I) combining (a) a feedstock comprising (i) milled corn grain and (ii) enzyme active whole soybean or enzyme active de-hulled soybean comprising endogenous urease, (b) urea, (c) a microorganism, and (d) water in a fermenter; and
    (II) fermenting the contents of the fermenter;
    wherein the enzyme active whole soybean or enzyme active de-hulled soybean is not exposed to temperatures greater than 71° C.; and
    wherein the fermentation efficiency is improved relative to the fermentation efficiency achieved in the absence of urea and urease.

16. The method of claim 15, wherein the improved fermentation efficiency provides at least one benefit selected from the group consisting of:
    (a) increased ethanol production;
    (b) decreased residual starch;
    (c) increased quantity of dried distillers grains (DDG);
    (d) higher protein content DDG;
    (e) improved essential amino acid profile of DDG;
    (f) increased oil recovery;
    (g) decreased DDG pigmentation; and
    (h) increased fiber conversion.

17. The method of claim 15, wherein the feedstock comprises 90.00% to 99.95% w/w milled corn grain and 0.05% to 10.00% w/w enzyme active whole soybean or enzyme active dehulled soybean.

18. The method of claim 17, wherein the enzyme active whole soybean or enzyme active dehulled soybean is enzyme active soy flour.

19. The method of claim 17, wherein the enzyme active whole soybean or enzyme active dehulled soybean is uncooked.

20. The method of claim 15, wherein the microorganism is yeast.

* * * * *